(12) United States Patent
Ezquerro Saenz et al.

(10) Patent No.: US 7,057,013 B1
(45) Date of Patent: Jun. 6, 2006

(54) TGFβ1 INHIBITOR PEPTIDES

(75) Inventors: Ignacio José Ezquerro Saenz, Pamplona (ES); Juan José Lasarte Sagastibelza, Berriozar (ES); Jesús Prieto Valtueña, Pamplona (ES); Francisco Borras Cuesta, Pamplona (ES)

(73) Assignee: Proyecto de Biomedicina Cima, S.L., Pamplona (ES)

( * ) Notice: Subject to any disclaimer, the term of this patent is extended or adjusted under 35 U.S.C. 154(b) by 0 days.

(21) Appl. No.: 09/831,253

(22) PCT Filed: Nov. 23, 1999

(86) PCT No.: PCT/ES99/00375

§ 371 (c)(1),
(2), (4) Date: Jun. 27, 2001

(87) PCT Pub. No.: WO00/31135

PCT Pub. Date: Jun. 2, 2000

(30) Foreign Application Priority Data

Nov. 24, 1998 (ES) .................................... 9802465

(51) Int. Cl.
*A61K 48/00* (2006.01)

(52) U.S. Cl. ...................................... 530/326; 530/327

(58) Field of Classification Search ................ 530/326, 530/327

See application file for complete search history.

(56) References Cited

U.S. PATENT DOCUMENTS 5,650,494 A * 7/1997 Cerletti et al. .............. 530/399

FOREIGN PATENT DOCUMENTS

WO 96/25178 * 8/1996

OTHER PUBLICATIONS

Attwood, Science 2000; 290:p. 471-473.*
Skolnick et al. Trends in Biotech. 2000;18(1): p. 34-39.*
Metzler et al. Nature Structural Biol. 1997; 4:527-531, QH 506.N4.*

* cited by examiner

*Primary Examiner*—Patrick J. Nolan
*Assistant Examiner*—Yunsoo Kim
(74) *Attorney, Agent, or Firm*—Ladas & Parry LLP

(57) ABSTRACT

Antagonistic synthetic peptides, obtained from TGFβ1 or from its receptors in the organism, that can be used in the manufacture, both on their own, as well as the gene sequences that encode them and the recombinant systems that express them, in the manufacture of compositions for use in the treatment of liver diseases and more concretely in cases of fibrosis. The said compositions can optionally include mimotopes of the said active peptides.

11 Claims, 28 Drawing Sheets

SEQUENCE LISTING

```
<160> NUMBER OF SEQ ID NOS: 178

<210> SEQ ID NO 1
<211> LENGTH: 15
<212> TYPE: PRT
<213> ORGANISM: Artificial sequence
<220> FEATURE:
<223> OTHER INFORMATION: Derived from human TGB beta 1 position 319-333

<400> SEQUENCE: 1

His Ala Asn Phe Cys Leu Gly Pro Cys Pro Tyr Ile Trp Ser Leu
1               5                   10                  15

<210> SEQ ID NO 2
<211> LENGTH: 14
<212> TYPE: PRT
<213> ORGANISM: Artificial sequence
<220> FEATURE:
<223> OTHER INFORMATION: Derived from human TGB beta 1 position 322-335

<400> SEQUENCE: 2

Phe Cys Leu Gly Pro Cys Pro Tyr Ile Trp Ser Leu Asp Thr
1               5                   10

<210> SEQ ID NO 3
<211> LENGTH: 12
<212> TYPE: PRT
<213> ORGANISM: Artificial sequence
<220> FEATURE:
<223> OTHER INFORMATION: Derived from rat TGB beta 1 type III receptor
      position 731-742

<400> SEQUENCE: 3

Thr Ser Leu Asp Ala Thr Met Ile Trp Thr Met Met
1               5                   10

<210> SEQ ID NO 4
<211> LENGTH: 15
<212> TYPE: PRT
<213> ORGANISM: Artificial sequence
<220> FEATURE:
<223> OTHER INFORMATION: Derived from human TGB beta 1 position 245-259

<400> SEQUENCE: 4

Ser Asn Pro Tyr Ser Ala Phe Gln Val Asp Ile Ile Val Asp Ile
1               5                   10                  15

<210> SEQ ID NO 5
```

```
<211> LENGTH: 9
<212> TYPE: PRT
<213> ORGANISM: Artificial sequence
<220> FEATURE:
<223> OTHER INFORMATION: Synthetic peptide derived from P54

<400> SEQUENCE: 5

Thr Ser Leu Met Ile Trp Thr Met Met
1               5

<210> SEQ ID NO 6
<211> LENGTH: 14
<212> TYPE: PRT
<213> ORGANISM: Artificial sequence
<220> FEATURE:
<223> OTHER INFORMATION: Synthetic peptide from human TGB beta 1 type
      III receptor, position 729-742

<400> SEQUENCE: 6

Thr Ser Leu Asp Ala Ser Ile Ile Trp Ala Met Met Gln Asn
1               5                   10

<210> SEQ ID NO 7
<211> LENGTH: 14
<212> TYPE: PRT
<213> ORGANISM: Artificial sequence
<220> FEATURE:
<223> OTHER INFORMATION: Synthetic peptide from human TGB beta 1 type
      III receptor, position 241-254

<400> SEQUENCE: 7

Ser Asn Pro Tyr Ser Ala Phe Gln Val Asp Ile Thr Ile Asp
1               5                   10

<210> SEQ ID NO 8
<211> LENGTH: 15
<212> TYPE: PRT
<213> ORGANISM: Artificial sequence
<220> FEATURE:
<223> OTHER INFORMATION: Synthetic peptide from pig endoglin, position
      247-261

<400> SEQUENCE: 8

Glu Ala Val Leu Ile Leu Gln Gly Pro Pro Tyr Val Ser Trp Leu
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Synthetic peptide from pig endoglin, position
      445-459

<400> SEQUENCE: 9

Leu Asp Ser Leu Ser Phe Gln Leu Gly Leu Tyr Leu Ser Pro His
1               5                   10                  15

<210> SEQ ID NO 10
<211> LENGTH: 23
<212> TYPE: PRT
<213> ORGANISM: Artificial sequence
<220> FEATURE:
<223> OTHER INFORMATION: Synthetic peptide from human TGB beta 1,
      position 313-335

<400> SEQUENCE: 10

His Glu Pro Lys Gly Tyr His Ala Asn Phe Cys Leu Gly Pro Cys Pro
```

```
1               5                  10                 15
Tyr Ile Trp Ser Leu Asp Thr
                  20

<210> SEQ ID NO 11
<211> LENGTH: 14
<212> TYPE: PRT
<213> ORGANISM: Artificial sequence
<220> FEATURE:
<223> OTHER INFORMATION: Synthetic peptide from human TGB beta 1,
      position 2810-293

<400> SEQUENCE: 11

Ala Leu Asp Thr Asn Tyr Cys Phe Ser Ser Thr Glu Lys Asn
1               5                  10

<210> SEQ ID NO 12
<211> LENGTH: 13
<212> TYPE: PRT
<213> ORGANISM: Artificial sequence
<220> FEATURE:
<223> OTHER INFORMATION: Synthetic peptide from human TGB beta 1,
      position 284-297

<400> SEQUENCE: 12

Asn Tyr Cys Ser Ser Thr Glu Lys Asn Cys Cys Val Arg
1               5                  10

<210> SEQ ID NO 13
<211> LENGTH: 14
<212> TYPE: PRT
<213> ORGANISM: Artificial sequence
<220> FEATURE:
<223> OTHER INFORMATION: Synthetic peptide from human TGB beta 1,
      position 288-301

<400> SEQUENCE: 13

Ser Ser Thr Glu Lys Asn Cys Cys Val Arg Gln Leu Tyr Ile
1               5                  10

<210> SEQ ID NO 14
<211> LENGTH: 14
<212> TYPE: PRT
<213> ORGANISM: Artificial sequence
<220> FEATURE:
<223> OTHER INFORMATION: Synthetic peptide from human TGB beta 1,
      position 294-307

<400> SEQUENCE: 14

Cys Cys Val Arg Gln Leu Tyr Ile Asp Phe Arg Lys Asp Leu
1               5                  10

<210> SEQ ID NO 15
<211> LENGTH: 14
<212> TYPE: PRT
<213> ORGANISM: Artificial sequence
<220> FEATURE:
<223> OTHER INFORMATION: Synthetic peptide from human TGB beta 1,
      position 298-311

<400> SEQUENCE: 15

Gln Leu Tyr Ile Asp Phe Arg Lys Asp Leu Gly Trp Lys Trp
1               5                  10

<210> SEQ ID NO 16
<211> LENGTH: 14
<212> TYPE: PRT
```

```
<213> ORGANISM: Artificial sequence
<220> FEATURE:
<223> OTHER INFORMATION: Synthetic peptide from human TGB beta 1,
      position 302-315

<400> SEQUENCE: 16

Asp Phe Arg Lys Asp Leu Gly Trp Lys Trp Ile His Glu Pro
1               5                   10

<210> SEQ ID NO 17
<211> LENGTH: 14
<212> TYPE: PRT
<213> ORGANISM: Artificial sequence
<220> FEATURE:
<223> OTHER INFORMATION: Synthetic peptide from human TGB beta 1,
      position 306-319

<400> SEQUENCE: 17

Asp Leu Gly Trp Lys Trp Ile His Glu Pro Lys Gly Tyr His
1               5                   10

<210> SEQ ID NO 18
<211> LENGTH: 14
<212> TYPE: PRT
<213> ORGANISM: Artificial sequence
<220> FEATURE:
<223> OTHER INFORMATION: Synthetic peptide from human TGB beta 1,
      position 308-321

<400> SEQUENCE: 18

Gly Trp Lys Trp Ile His Glu Pro Lys Gly Tyr His Ala Asn
1               5                   10

<210> SEQ ID NO 19
<211> LENGTH: 14
<212> TYPE: PRT
<213> ORGANISM: Artificial sequence
<220> FEATURE:
<223> OTHER INFORMATION: Synthetic peptide from human TGB beta 1,
      position 312-325

<400> SEQUENCE: 19

Ile His Glu Pro Lys Gly Tyr His Ala Asn Phe Cys Leu Gly
1               5                   10

<210> SEQ ID NO 20
<211> LENGTH: 14
<212> TYPE: PRT
<213> ORGANISM: Artificial sequence
<220> FEATURE:
<223> OTHER INFORMATION: Synthetic peptide from human TGB beta 1,
      position 316-329

<400> SEQUENCE: 20

Lys Gly Tyr His Ala Asn Phe Cys Leu Gly Pro Cys Pro Tyr
1               5                   10

<210> SEQ ID NO 21
<211> LENGTH: 14
<212> TYPE: PRT
<213> ORGANISM: Artificial sequence
<220> FEATURE:
<223> OTHER INFORMATION: Synthetic peptide from human TGB beta 1,
      position 326-339

<400> SEQUENCE: 21

Pro Cys Pro Tyr Ile Trp Ser Leu Asp Thr Gln Tyr Ser Lys
1               5                   10
```

-continued

<210> SEQ ID NO 22
<211> LENGTH: 14
<212> TYPE: PRT
<213> ORGANISM: Artificial sequence
<220> FEATURE:
<223> OTHER INFORMATION: Synthetic peptide from human TGB beta 1,
      position 330-343

<400> SEQUENCE: 22

Ile Trp Ser Leu Asp Thr Gln Tyr Ser Lys Val Leu Ala Leu
1               5                   10

<210> SEQ ID NO 23
<211> LENGTH: 15
<212> TYPE: PRT
<213> ORGANISM: Artificial sequence
<220> FEATURE:
<223> OTHER INFORMATION: Synthetic peptide from human TGB beta 1,
      position 335-349

<400> SEQUENCE: 23

Thr Gln Tyr Ser Lys Val Leu Ala Leu Tyr Asn Gln His Asn Pro
1               5                   10                  15

<210> SEQ ID NO 24
<211> LENGTH: 14
<212> TYPE: PRT
<213> ORGANISM: Artificial sequence
<220> FEATURE:
<223> OTHER INFORMATION: Synthetic peptide from human TGB beta 1,
      position 336-349

<400> SEQUENCE: 24

Gln Tyr Ser Lys Val Leu Ala Leu Tyr Asn Gln His Asn Pro
1               5                   10

<210> SEQ ID NO 25
<211> LENGTH: 14
<212> TYPE: PRT
<213> ORGANISM: Artificial sequence
<220> FEATURE:
<223> OTHER INFORMATION: Synthetic peptide from human TGB beta 1,
      position 340-353

<400> SEQUENCE: 25

Val Leu Ala Leu Tyr Asn Gln His Asn Pro Gly Ala Ser Ala
1               5                   10

<210> SEQ ID NO 26
<211> LENGTH: 15
<212> TYPE: PRT
<213> ORGANISM: Artificial sequence
<220> FEATURE:
<223> OTHER INFORMATION: Synthetic peptide from human TGB beta 1,
      position 343-358

<400> SEQUENCE: 26

Leu Tyr Asn Gln His Asn Pro Gly Ala Ser Ala Ala Pro Cys Cys
1               5                   10                  15

<210> SEQ ID NO 27
<211> LENGTH: 14
<212> TYPE: PRT
<213> ORGANISM: Artificial sequence
<220> FEATURE:
<223> OTHER INFORMATION: Synthetic peptide from human TGB beta 1,
      position 348-360

-continued

<400> SEQUENCE: 27

Tyr Asn Gln His Asn Pro Gly Ala Ser Ala Ala Pro Cys Cys
1               5                   10

<210> SEQ ID NO 28
<211> LENGTH: 13
<212> TYPE: PRT
<213> ORGANISM: Artificial sequence
<220> FEATURE:
<223> OTHER INFORMATION: Synthetic peptide from human TGB beta 1,
      position 344-358

<400> SEQUENCE: 28

Asn Pro Gly Ala Ser Ala Ala Pro Cys Cys Val Pro Gln
1               5                   10

<210> SEQ ID NO 29
<211> LENGTH: 14
<212> TYPE: PRT
<213> ORGANISM: Artificial sequence
<220> FEATURE:
<223> OTHER INFORMATION: Synthetic peptide from human TGB beta 1,
      position 348-360

<400> SEQUENCE: 29

Gly Ala Ser Ala Ala Pro Cys Cys Val Pro Gln Ala Leu Glu
1               5                   10

<210> SEQ ID NO 30
<211> LENGTH: 14
<212> TYPE: PRT
<213> ORGANISM: Artificial sequence
<220> FEATURE:
<223> OTHER INFORMATION: Synthetic peptide from human TGB beta 1,
      position 354-367

<400> SEQUENCE: 30

Ala Pro Cys Cys Val Pro Gln Ala Leu Glu Pro Leu Pro Ile
1               5                   10

<210> SEQ ID NO 31
<211> LENGTH: 14
<212> TYPE: PRT
<213> ORGANISM: Artificial sequence
<220> FEATURE:
<223> OTHER INFORMATION: Synthetic peptide from human TGB beta 1,
      position 358-371

<400> SEQUENCE: 31

Val Pro Gln Ala Leu Glu Pro Leu Pro Ile Val Tyr Tyr Val
1               5                   10

<210> SEQ ID NO 32
<211> LENGTH: 14
<212> TYPE: PRT
<213> ORGANISM: Artificial sequence
<220> FEATURE:
<223> OTHER INFORMATION: Synthetic peptide from human TGB beta 1,
      position 364-377

<400> SEQUENCE: 32

Pro Leu Pro Ile Val Tyr Tyr Val Gly Arg Lys Pro Lys Val
1               5                   10

<210> SEQ ID NO 33
<211> LENGTH: 14

```
<212> TYPE: PRT
<213> ORGANISM: Artificial sequence
<220> FEATURE:
<223> OTHER INFORMATION: Synthetic peptide from human TGB beta 1,
      position 368-381

<400> SEQUENCE: 33

Val Tyr Tyr Val Gly Arg Lys Pro Lys Val Glu Gln Leu Ser
1               5                   10

<210> SEQ ID NO 34
<211> LENGTH: 14
<212> TYPE: PRT
<213> ORGANISM: Artificial sequence
<220> FEATURE:
<223> OTHER INFORMATION: Synthetic peptide from human TGB beta 1,
      position 372-385

<400> SEQUENCE: 34

Gly Arg Lys Pro Lys Val Glu Gln Leu Ser Asn Met Ile Val
1               5                   10

<210> SEQ ID NO 35
<211> LENGTH: 14
<212> TYPE: PRT
<213> ORGANISM: Artificial sequence
<220> FEATURE:
<223> OTHER INFORMATION: Synthetic peptide from human TGB beta 1,
      position 378-391

<400> SEQUENCE: 35

Glu Gln Leu Ser Asn Met Ile Val Arg Ser Cys Lys Cys Ser
1               5                   10

<210> SEQ ID NO 36
<211> LENGTH: 21
<212> TYPE: PRT
<213> ORGANISM: Artificial sequence
<220> FEATURE:
<223> OTHER INFORMATION: Synthetic peptide from human TGB beta 1,
      position 322-344

<400> SEQUENCE: 36

Phe Cys Leu Gly Pro Cys Pro Tyr Ile Trp Ser Leu Asp Thr Gln Lys
1               5                   10                  15

Val Leu Ala Leu Tyr
            20

<210> SEQ ID NO 37
<211> LENGTH: 14
<212> TYPE: PRT
<213> ORGANISM: Artificial sequence
<220> FEATURE:
<223> OTHER INFORMATION: Synthetic peptide from human TGB beta 1,
      position 322-335

<400> SEQUENCE: 37

Phe Ser Leu Gly Pro Cys Pro Tyr Ile Trp Ser Leu Asp Thr
1               5                   10

<210> SEQ ID NO 38
<211> LENGTH: 14
<212> TYPE: PRT
<213> ORGANISM: Artificial sequence
<220> FEATURE:
<223> OTHER INFORMATION: Synthetic peptide from human TGB beta 1,
      position 322-335
```

-continued

```
<400> SEQUENCE: 38

Phe Cys Leu Gly Pro Ser Pro Tyr Ile Trp Ser Leu Asp Thr
1               5                   10

<210> SEQ ID NO 39
<211> LENGTH: 14
<212> TYPE: PRT
<213> ORGANISM: Artificial sequence
<220> FEATURE:
<223> OTHER INFORMATION: Synthetic peptide from human TGB beta 1,
      position 322-335

<400> SEQUENCE: 39

Phe Ser Leu Gly Pro Ser Pro Tyr Ile Trp Ser Leu Asp Thr
1               5                   10

<210> SEQ ID NO 40
<211> LENGTH: 14
<212> TYPE: PRT
<213> ORGANISM: Artificial sequence
<220> FEATURE:
<223> OTHER INFORMATION: Synthetic peptide from human TGB beta 1,
      position 322-335

<400> SEQUENCE: 40

Phe Cys Leu Gly Pro Cys Pro Tyr Ile Trp Ser Asp Asp Asp
1               5                   10

<210> SEQ ID NO 41
<211> LENGTH: 14
<212> TYPE: PRT
<213> ORGANISM: Artificial sequence
<220> FEATURE:
<223> OTHER INFORMATION: Synthetic peptide modified from human TGB beta
      1, position 322-335

<400> SEQUENCE: 41

Asp Asp Asp Gly Pro Cys Pro Tyr Ile Trp Ser Leu Asp Thr
1               5                   10

<210> SEQ ID NO 42
<211> LENGTH: 14
<212> TYPE: PRT
<213> ORGANISM: Artificial sequence
<220> FEATURE:
<223> OTHER INFORMATION: Synthetic peptide modified from human TGB
      beta 1, position 322-335

<400> SEQUENCE: 42

Asp Asp Asp Gly Pro Cys Pro Tyr Ile Trp Ser Asp Asp Asp
1               5                   10

<210> SEQ ID NO 43
<211> LENGTH: 11
<212> TYPE: PRT
<213> ORGANISM: Artificial sequence
<220> FEATURE:
<223> OTHER INFORMATION: Synthetic peptide modified from human TGB
      beta 1, position 325-332

<400> SEQUENCE: 43

Gly Pro Cys Pro Tyr Ile Trp Ser Asp Asp Asp
1               5                   10

<210> SEQ ID NO 44
<211> LENGTH: 11
<212> TYPE: PRT
```

```
<213> ORGANISM: Artificial sequence
<220> FEATURE:
<223> OTHER INFORMATION: Synthetic peptide modified from human TGB
      beta 1, position 325-335

<400> SEQUENCE: 44

Asp Asp Asp Gly Pro Cys Pro Tyr Ile Trp Ser
1               5                   10

<210> SEQ ID NO 45
<211> LENGTH: 10
<212> TYPE: PRT
<213> ORGANISM: Artificial sequence
<220> FEATURE:
<223> OTHER INFORMATION: Synthetic peptide modified from human TGB
      beta 1, position 325-332

<400> SEQUENCE: 45

Asp Gly Pro Cys Pro Tyr Ile Trp Ser Asp
1               5                   10

<210> SEQ ID NO 46
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 91-102

<400> SEQUENCE: 46

Asn Pro Ile Ala Ser Val His Thr His His Lys Pro
1               5                   10

<210> SEQ ID NO 47
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 104-115

<400> SEQUENCE: 47

Val Phe Leu Leu Asn Ser Pro Gln Pro Leu Val Trp
1               5                   10

<210> SEQ ID NO 48
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 109-120

<400> SEQUENCE: 48

Ser Pro Gln Pro Leu Val Trp His Leu Lys Thr Glu
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 110-121

<400> SEQUENCE: 49

Pro Gln Pro Leu Val Trp His Leu Lys Thr Glu Arg
1               5                   10
```

<210> SEQ ID NO 50
<211> LENGTH: 12
<212> TYPE: PRT
<213> ORGANISM: Artificial sequence
<220> FEATURE:
<223> OTHER INFORMATION: Synthetic peptide from rat TGB beta 1 type III receptor, position 333-344

<400> SEQUENCE: 50

Trp Ala Leu Asp Asn Gly Tyr Arg Pro Val Thr Ser
1               5                   10

<210> SEQ ID NO 51
<211> LENGTH: 12
<212> TYPE: PRT
<213> ORGANISM: Artificial sequence
<220> FEATURE:
<223> OTHER INFORMATION: Synthetic peptide from rat TGB beta 1 type III receptor, position 428-349

<400> SEQUENCE: 51

Pro Ile Val Pro Ser Val Gln Leu Leu Pro Asp His
1               5                   10

<210> SEQ ID NO 52
<211> LENGTH: 12
<212> TYPE: PRT
<213> ORGANISM: Artificial sequence
<220> FEATURE:
<223> OTHER INFORMATION: Synthetic peptide from rat TGB beta 1 type III receptor, position 555-566

<400> SEQUENCE: 52

Gly Asp Glu Gly Glu Thr Ala Pro Leu Ser Arg Ala
1               5                   10

<210> SEQ ID NO 53
<211> LENGTH: 12
<212> TYPE: PRT
<213> ORGANISM: Artificial sequence
<220> FEATURE:
<223> OTHER INFORMATION: Synthetic peptide from rat TGB beta 1 type III receptor, position 563-574

<400> SEQUENCE: 53

Leu Ser Arg Ala Gly Val Val Val Phe Asn Cys Ser
1               5                   10

<210> SEQ ID NO 54
<211> LENGTH: 12
<212> TYPE: PRT
<213> ORGANISM: Artificial sequence
<220> FEATURE:
<223> OTHER INFORMATION: Synthetic peptide from rat TGB beta 1 type III receptor, position 603-614

<400> SEQUENCE: 54

Leu Phe Leu Val Pro Ser Pro Gly Val Phe Ser Val
1               5                   10

<210> SEQ ID NO 55
<211> LENGTH: 12
<212> TYPE: PRT
<213> ORGANISM: Artificial sequence
<220> FEATURE:
<223> OTHER INFORMATION: Synthetic peptide from rat TGB beta 1 type III receptor, position 605-616

-continued

```
<400> SEQUENCE: 55

Leu Val Pro Ser Pro Gly Val Phe Ser Val Ala Glu
1               5                   10

<210> SEQ ID NO 56
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 707-718

<400> SEQUENCE: 56

Glu Leu Thr Leu Cys Ser Arg Lys Lys Gly Ser Leu
1               5                   10

<210> SEQ ID NO 57
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 712-723

<400> SEQUENCE: 57

Ser Arg Lys Lys Gly Ser Leu Lys Leu Pro Arg Cys
1               5                   10

<210> SEQ ID NO 58
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 717-728

<400> SEQUENCE: 58

Ser Leu Lys Leu Pro Arg Cys Val Thr Pro Asp Asp
1               5                   10

<210> SEQ ID NO 59
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 722-733

<400> SEQUENCE: 59

Arg Cys Val Thr Pro Asp Asp Ala Cys Thr Ser Leu
1               5                   10

<210> SEQ ID NO 60
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 727-738

<400> SEQUENCE: 60

Asp Asp Ala Cys Thr Ser Leu Asp Ala Thr Met Ile
1               5                   10

<210> SEQ ID NO 61
<211> LENGTH: 12
```

```
<212> TYPE: PRT
<213> ORGANISM: Artificial sequence
<220> FEATURE:
<223> OTHER INFORMATION: Synthetic peptide from rat TGB beta 1 type III
      receptor, position 732-743

<400> SEQUENCE: 61

Ser Leu Asp Ala Thr Met Ile Trp Thr Met Met Gln
1               5                   10

<210> SEQ ID NO 62
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 737-748

<400> SEQUENCE: 62

Met Ile Trp Thr Met Met Gln Asn Lys Lys Thr Phe
1               5                   10

<210> SEQ ID NO 63
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 742-752

<400> SEQUENCE: 63

Met Gln Asn Lys Lys Thr Phe Thr Lys Pro Leu Ala
1               5                   10

<210> SEQ ID NO 64
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 747-758

<400> SEQUENCE: 64

Thr Phe Thr Lys Pro Leu Ala Val Val Leu Gln Val
1               5                   10

<210> SEQ ID NO 65
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 761-775

<400> SEQUENCE: 65

Lys Glu Asn Val Pro Ser Thr Lys Asp Ser Ser Pro Ile Pro Pro
1               5                   10                  15

<210> SEQ ID NO 66
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 766-780

<400> SEQUENCE: 66

Ser Thr Lys Asp Ser Ser Pro Ile Pro Pro Pro Pro Pro Gln Ile
```

```
<210> SEQ ID NO 67
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 771-785

<400> SEQUENCE: 67

Ser Pro Ile Pro Pro Pro Pro Gln Ile Phe His Gly Leu Asp
1               5                   10                  15

<210> SEQ ID NO 68
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 776-790

<400> SEQUENCE: 68

Pro Pro Pro Gln Ile Phe His Gly Leu Asp Thr Leu Thr Val Met
1               5                   10                  15

<210> SEQ ID NO 69
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 781-795

<400> SEQUENCE: 69

Phe His Gly Leu Asp Thr Leu Thr Val Met Gly Ile Ala Phe Ala
1               5                   10                  15

<210> SEQ ID NO 70
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 786-800

<400> SEQUENCE: 70

Thr Leu Thr Val Met Gly Ile Ala Phe Ala Ala Phe Val Ile Gly
1               5                   10                  15

<210> SEQ ID NO 71
<211> LENGTH: 12
<212> TYPE: PRT
<213> ORGANISM: Artificial sequence
<220> FEATURE:
<223> OTHER INFORMATION: Synthetic peptide from rat TGB beta 1 type III
      receptor, position 797-809

<400> SEQUENCE: 71

Leu Leu Thr Gly Ala Leu Trp Tyr Ile Tyr Ser His
1               5                   10

<210> SEQ ID NO 72
<211> LENGTH: 15
<212> TYPE: PRT
<213> ORGANISM: Artificial sequence
<220> FEATURE:
<223> OTHER INFORMATION: Synthetic peptide from rat TGB beta 1 type III
```

-continued receptor, position 45-59

<400> SEQUENCE: 72

Leu Met Glu Ser Phe Thr Val Leu Ser Gly Cys Ala Ser Arg Gly
1               5                   10                  15

<210> SEQ ID NO 73
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 50-64

<400> SEQUENCE: 73

Thr Val Leu Ser Gly Cys Ala Ser Arg Gly Thr Thr Gly Leu Pro
1               5                   10                  15

<210> SEQ ID NO 74
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 55-69

<400> SEQUENCE: 74

Cys Ala Ser Arg Gly Thr Thr Gly Leu Pro Arg Glu Val His Val
1               5                   10                  15

<210> SEQ ID NO 75
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 60-74

<400> SEQUENCE: 75

Thr Thr Gly Leu Pro Arg Glu Val His Val Leu Asn Leu Arg Ser
1               5                   10                  15

<210> SEQ ID NO 76
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 65-79

<400> SEQUENCE: 76

Arg Glu Val His Val Leu Asn Leu Arg Ser Thr Asp Gln Gly Pro
1               5                   10                  15

<210> SEQ ID NO 77
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 70-84

<400> SEQUENCE: 77

Leu Asn Leu Arg Ser Thr Asp Gln Gly Pro Gly Gln Arg Gln Arg
1               5                   10                  15

<210> SEQ ID NO 78

```
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 75-89

<400> SEQUENCE: 78

Thr Asp Gln Gly Pro Gly Gln Arg Gln Arg Glu Val Thr Leu His
1               5                   10                  15

<210> SEQ ID NO 79
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 80-94

<400> SEQUENCE: 79

Gly Gln Arg Gln Arg Glu Val Thr Leu His Leu Asn Pro Ile Ala
1               5                   10                  15

<210> SEQ ID NO 80
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 85-99

<400> SEQUENCE: 80

Glu Val Thr Leu His Leu Asn Pro Ile Ala Ser Val His Thr His
1               5                   10                  15

<210> SEQ ID NO 81
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 90-104

<400> SEQUENCE: 81

Leu Asn Pro Ile Ala Ser Val His Thr His His Lys Pro Ile Val
1               5                   10                  15

<210> SEQ ID NO 82
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 95-109

<400> SEQUENCE: 82

Ser Val His Thr His His Lys Pro Ile Val Phe Leu Leu Asn Ser
1               5                   10                  15

<210> SEQ ID NO 83
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 100-114

<400> SEQUENCE: 83
```

-continued

His Lys Pro Ile Val Phe Leu Leu Asn Ser Pro Gln Pro Leu Val
1               5                   10                  15

<210> SEQ ID NO 84
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 105-119

<400> SEQUENCE: 84

Phe Leu Leu Asn Ser Pro Gln Pro Leu Val Trp His Leu Lys Thr
1               5                   10                  15

<210> SEQ ID NO 85
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 110-124

<400> SEQUENCE: 85

Pro Gln Pro Leu Val Trp His Leu Lys Thr Glu Arg Leu Ala Ala
1               5                   10                  15

<210> SEQ ID NO 86
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 115-129

<400> SEQUENCE: 86

Trp His Leu Lys Thr Glu Arg Leu Ala Ala Gly Val Pro Arg Leu
1               5                   10                  15

<210> SEQ ID NO 87
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 120-134

<400> SEQUENCE: 87

Arg Leu Ala Ala Gly Val Pro Arg Leu Phe Leu Val Ser Glu Gly
1               5                   10                  15

<210> SEQ ID NO 88
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 125-139

<400> SEQUENCE: 88

Gly Val Pro Arg Leu Phe Leu Val Ser Glu Gly Ser Val Val Gln
1               5                   10                  15

<210> SEQ ID NO 89
<211> LENGTH: 15
<212> TYPE: PRT
<213> ORGANISM: Artificial sequence
<220> FEATURE:

-continued

<223> OTHER INFORMATION: Synthetic peptide from rat TGB beta 1 type III
     receptor, position 130-144

<400> SEQUENCE: 89

Phe Leu Val Ser Glu Gly Ser Val Val Gln Phe Pro Ser Gly Asn
1               5                   10                  15

<210> SEQ ID NO 90
<211> LENGTH: 15
<212> TYPE: PRT
<213> ORGANISM: Artificial sequence
<220> FEATURE:
<223> OTHER INFORMATION: Synthetic peptide from rat TGB beta 1 type III
     receptor, position 135-149

<400> SEQUENCE: 90

Gly Ser Val Val Gln Phe Pro Ser Gly Asn Phe Ser Leu Thr Ala
1               5                   10                  15

<210> SEQ ID NO 91
<211> LENGTH: 15
<212> TYPE: PRT
<213> ORGANISM: Artificial sequence
<220> FEATURE:
<223> OTHER INFORMATION: Synthetic peptide from rat TGB beta 1 type III
     receptor, position 140-154

<400> SEQUENCE: 91

Phe Pro Ser Gly Asn Phe Ser Leu Thr Ala Glu Thr Glu Glu Arg
1               5                   10                  15

<210> SEQ ID NO 92
<211> LENGTH: 15
<212> TYPE: PRT
<213> ORGANISM: Artificial sequence
<220> FEATURE:
<223> OTHER INFORMATION: Synthetic peptide from rat TGB beta 1 type III
     receptor, position 145-159

<400> SEQUENCE: 92

Phe Ser Leu Thr Ala Glu Thr Glu Glu Arg Asn Phe Pro Gln Glu
1               5                   10                  15

<210> SEQ ID NO 93
<211> LENGTH: 15
<212> TYPE: PRT
<213> ORGANISM: Artificial sequence
<220> FEATURE:
<223> OTHER INFORMATION: Synthetic peptide from rat TGB beta 1 type III
     receptor, position 150-164

<400> SEQUENCE: 93

Glu Thr Glu Glu Arg Asn Phe Pro Gln Glu Asn Glu His Leu Val
1               5                   10                  15

<210> SEQ ID NO 94
<211> LENGTH: 15
<212> TYPE: PRT
<213> ORGANISM: Artificial sequence
<220> FEATURE:
<223> OTHER INFORMATION: Synthetic peptide from rat TGB beta 1 type III
     receptor, position 155-169

<400> SEQUENCE: 94

Asn Phe Pro Gln Glu Asn Glu His Leu Val Arg Trp Ala Gln Lys
1               5                   10                  15

```
<210> SEQ ID NO 95
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 160-174

<400> SEQUENCE: 95

Asn Glu His Leu Val Arg Trp Ala Gln Lys Glu Tyr Gly Ala Val
1               5                   10                  15

<210> SEQ ID NO 96
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 165-179

<400> SEQUENCE: 96

Arg Trp Ala Gln Lys Glu Tyr Gly Ala Val Thr Ser Phe Thr Glu
1               5                   10                  15

<210> SEQ ID NO 97
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 170-184

<400> SEQUENCE: 97

Glu Tyr Gly Ala Val Thr Ser Phe Thr Glu Leu Lys Ile Ala Arg
1               5                   10                  15

<210> SEQ ID NO 98
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 175-189

<400> SEQUENCE: 98

Thr Ser Phe Thr Glu Leu Lys Ile Ala Arg Asn Ile Tyr Ile Lys
1               5                   10                  15

<210> SEQ ID NO 99
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 180-194

<400> SEQUENCE: 99

Leu Lys Ile Ala Arg Asn Ile Tyr Ile Lys Val Gly Glu Asp Gln
1               5                   10                  15

<210> SEQ ID NO 100
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 185-199

<400> SEQUENCE: 100
```

Asn Ile Tyr Ile Lys Val Gly Glu Asp Gln Val Phe Pro Pro Thr
1               5                  10                 15

<210> SEQ ID NO 101
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 190-201

<400> SEQUENCE: 101

Val Gly Glu Asp Gln Val Phe Pro Pro Thr Cys Asn Ile Gly Lys
1               5                  10                 15

<210> SEQ ID NO 102
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 195-209

<400> SEQUENCE: 102

Val Phe Pro Pro Thr Cys Asn Ile Gly Lys Asn Phe Leu Ser Leu
1               5                  10                 15

<210> SEQ ID NO 103
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 200-214

<400> SEQUENCE: 103

Cys Asn Ile Gly Lys Asn Phe Leu Ser Leu Asn Tyr Leu Ala Glu
1               5                  10                 15

<210> SEQ ID NO 104
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 205-219

<400> SEQUENCE: 104

Asn Phe Leu Ser Leu Asn Tyr Leu Ala Glu Tyr Leu Gln Pro Lys
1               5                  10                 15

<210> SEQ ID NO 105
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 210-224

<400> SEQUENCE: 105

Asn Tyr Leu Ala Glu Tyr Leu Gln Pro Lys Ala Ala Glu Gly Cys
1               5                  10                 15

<210> SEQ ID NO 106
<211> LENGTH: 15
<212> TYPE: PRT
<213> ORGANISM: Artificial sequence

```
<220> FEATURE:
<223> OTHER INFORMATION: Synthetic peptide from rat TGB beta 1 type III
      receptor, position 215-229

<400> SEQUENCE: 106

Tyr Leu Gln Pro Lys Ala Ala Glu Gly Cys Val Leu Pro Ser Gln
1               5                   10                  15

<210> SEQ ID NO 107
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 220-234

<400> SEQUENCE: 107

Ala Ala Glu Gly Cys Val Leu Pro Ser Gln Pro His Glu Lys Glu
1               5                   10                  15

<210> SEQ ID NO 108
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 225-239

<400> SEQUENCE: 108

Val Leu Pro Ser Gln Pro His Glu Lys Glu Val His Ile Ile Glu
1               5                   10                  15

<210> SEQ ID NO 109
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 230-244

<400> SEQUENCE: 109

Pro His Glu Lys Glu Val His Ile Ile Glu Leu Ile Thr Pro Ser
1               5                   10                  15

<210> SEQ ID NO 110
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 235-249

<400> SEQUENCE: 110

Val His Ile Ile Glu Leu Ile Thr Pro Ser Ser Asn Pro Tyr Ser
1               5                   10                  15

<210> SEQ ID NO 111
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 240-254

<400> SEQUENCE: 111

Leu Ile Thr Pro Ser Ser Asn Pro Tyr Ser Ala Phe Gln Val Asp
1               5                   10                  15
```

<210> SEQ ID NO 112
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 250-264

<400> SEQUENCE: 112

Ala Phe Gln Val Asp Ile Ile Val Asp Ile Arg Pro Ala Gln Glu
1               5                   10                  15

<210> SEQ ID NO 113
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 255-269

<400> SEQUENCE: 113

Ile Ile Val Asp Ile Arg Pro Ala Gln Glu Asp Pro Glu Val Val
1               5                   10                  15

<210> SEQ ID NO 114
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 260-274

<400> SEQUENCE: 114

Arg Pro Ala Gln Glu Asp Pro Glu Val Val Lys Asn Leu Val Leu
1               5                   10                  15

<210> SEQ ID NO 115
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 265-279

<400> SEQUENCE: 115

Asp Pro Glu Val Val Lys Asn Leu Val Leu Ile Leu Lys Cys Lys
1               5                   10                  15

<210> SEQ ID NO 116
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 270-284

<400> SEQUENCE: 116

Lys Asn Leu Val Leu Ile Leu Lys Cys Lys Lys Ser Val Asn Trp
1               5                   10                  15

<210> SEQ ID NO 117
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 275-289

-continued

```
<400> SEQUENCE: 117

Ile Leu Lys Cys Lys Lys Ser Val Asn Trp Val Ile Lys Ser Phe
1               5                   10                  15

<210> SEQ ID NO 118
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 280-294

<400> SEQUENCE: 118

Lys Ser Val Asn Trp Val Ile Lys Ser Phe Asp Val Lys Gly Asn
1               5                   10                  15

<210> SEQ ID NO 119
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 285-299

<400> SEQUENCE: 119

Val Ile Lys Ser Phe Asp Val Lys Gly Asn Leu Lys Val Ile Ala
1               5                   10                  15

<210> SEQ ID NO 120
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 290-304

<400> SEQUENCE: 120

Asp Val Lys Gly Asn Leu Lys Val Ile Ala Pro Asn Ser Ile Gly
1               5                   10                  15

<210> SEQ ID NO 121
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 295-309

<400> SEQUENCE: 121

Leu Lys Val Ile Ala Pro Asn Ser Ile Gly Phe Gly Lys Glu Ser
1               5                   10                  15

<210> SEQ ID NO 122
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 300-314

<400> SEQUENCE: 122

Pro Asn Ser Ile Gly Phe Gly Lys Glu Ser Glu Arg Ser Met Thr
1               5                   10                  15

<210> SEQ ID NO 123
<211> LENGTH: 15
<212> TYPE: PRT
```

-continued

<213> ORGANISM: Artificial sequence
<220> FEATURE:
<223> OTHER INFORMATION: Synthetic peptide from rat TGB beta 1 type III
      receptor, position 305-319

<400> SEQUENCE: 123

Phe Gly Lys Glu Ser Glu Arg Ser Met Thr Met Thr Lys Leu Val
1               5                   10                  15

<210> SEQ ID NO 124
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 310-324

<400> SEQUENCE: 124

Glu Arg Ser Met Thr Met Thr Lys Leu Val Arg Asp Asp Ile Pro
1               5                   10                  15

<210> SEQ ID NO 125
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 325-329

<400> SEQUENCE: 125

Met Thr Lys Leu Val Arg Asp Asp Ile Pro Ser Thr Gln Glu Asn
1               5                   10                  15

<210> SEQ ID NO 126
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 320-334

<400> SEQUENCE: 126

Arg Asp Asp Ile Pro Ser Thr Gln Glu Asn Leu Met Lys Trp Ala
1               5                   10                  15

<210> SEQ ID NO 127
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 325-339

<400> SEQUENCE: 127

Ser Thr Gln Glu Asn Leu Met Lys Trp Ala Leu Asp Asn Gly Tyr
1               5                   10                  15

<210> SEQ ID NO 128
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 330-344

<400> SEQUENCE: 128

Leu Met Lys Trp Ala Leu Asp Asn Gly Tyr Arg Pro Val Thr Ser
1               5                   10                  15

-continued

<210> SEQ ID NO 129
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 335-349

<400> SEQUENCE: 129

Leu Asp Asn Gly Tyr Arg Pro Val Thr Ser Tyr Thr Met Ala Pro
1               5                   10                  15

<210> SEQ ID NO 130
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 340-354

<400> SEQUENCE: 130

Arg Pro Val Thr Ser Tyr Thr Met Ala Pro Val Ala Asn Arg Phe
1               5                   10                  15

<210> SEQ ID NO 131
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 345-359

<400> SEQUENCE: 131

Tyr Thr Met Ala Pro Val Ala Asn Arg Phe His Leu Arg Leu Glu
1               5                   10                  15

<210> SEQ ID NO 132
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 350-364

<400> SEQUENCE: 132

Val Ala Asn Arg Phe His Leu Arg Leu Glu Asn Asn Glu Glu Met
1               5                   10                  15

<210> SEQ ID NO 133
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 355-369

<400> SEQUENCE: 133

His Leu Arg Leu Glu Asn Asn Glu Glu Met Arg Asp Glu Glu Val
1               5                   10                  15

<210> SEQ ID NO 134
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 360-374

```
<400> SEQUENCE: 134

Asn Asn Glu Glu Met Arg Asp Glu Glu Val His Thr Ile Pro Pro
1               5                   10                  15

<210> SEQ ID NO 135
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 365-369

<400> SEQUENCE: 135

Arg Asp Glu Glu Val His Thr Ile Pro Pro Glu Leu Arg Ile Leu
1               5                   10                  15

<210> SEQ ID NO 136
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 370-384

<400> SEQUENCE: 136

His Thr Ile Pro Pro Glu Leu Arg Ile Leu Leu Asp Pro Asp His
1               5                   10                  15

<210> SEQ ID NO 137
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 375-389

<400> SEQUENCE: 137

Glu Leu Arg Ile Leu Leu Asp Pro Asp His Pro Pro Ala Leu Asp
1               5                   10                  15

<210> SEQ ID NO 138
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 380-394

<400> SEQUENCE: 138

Leu Asp Pro Asp His Pro Pro Ala Leu Asp Asn Pro Leu Phe Pro
1               5                   10                  15

<210> SEQ ID NO 139
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 385-399

<400> SEQUENCE: 139

Pro Pro Ala Leu Asp Asn Pro Leu Phe Pro Gly Glu Gly Ser Pro
1               5                   10                  15

<210> SEQ ID NO 140
<211> LENGTH: 15
```

```
<212> TYPE: PRT
<213> ORGANISM: Artificial sequence
<220> FEATURE:
<223> OTHER INFORMATION: Synthetic peptide from rat TGB beta 1 type III
      receptor, position 390-404

<400> SEQUENCE: 140

Asn Pro Leu Phe Pro Gly Glu Gly Ser Pro Asn Gly Gly Leu Pro
1               5                   10                  15

<210> SEQ ID NO 141
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 395-409

<400> SEQUENCE: 141

Gly Glu Gly Ser Pro Asn Gly Gly Leu Pro Phe Pro Phe Pro Asp
1               5                   10                  15

<210> SEQ ID NO 142
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 400-414

<400> SEQUENCE: 142

Asn Gly Gly Leu Pro Phe Pro Phe Pro Asp Ile Pro Arg Arg Gly
1               5                   10                  15

<210> SEQ ID NO 143
<211> LENGTH: 15
<212> TYPE: PRT
<213> ORGANISM: Artificial sequence
<220> FEATURE:
<223> OTHER INFORMATION: Synthetic peptide from rat TGB beta 1 type III
      receptor, position 405-419

<400> SEQUENCE: 143

Phe Pro Phe Pro Asp Ile Pro Arg Arg Gly Trp Lys Glu Gly Glu
1               5                   10                  15

<210> SEQ ID NO 144
<211> LENGTH: 12
<212> TYPE: PRT
<213> ORGANISM: Artificial sequence
<220> FEATURE:
<223> OTHER INFORMATION: Modified synthetic peptide from rat TGB beta 1
      type III receptor, position 731-742

<400> SEQUENCE: 144

Thr Ser Leu Asp Ala Thr Met Ile Trp Asp Asp Asp
1               5                   10

<210> SEQ ID NO 145
<211> LENGTH: 11
<212> TYPE: PRT
<213> ORGANISM: Artificial sequence
<220> FEATURE:
<223> OTHER INFORMATION: Modified synthetic peptide from rat TGB beta 1
      type III receptor, position 731-742

<400> SEQUENCE: 145

Asp Asp Asp Ala Thr Met Ile Trp Thr Met Met
```

-continued

```
<210> SEQ ID NO 146
<211> LENGTH: 7
<212> TYPE: PRT
<213> ORGANISM: Artificial sequence
<220> FEATURE:
<223> OTHER INFORMATION: Modified synthetic peptide from rat TGB beta 1
      type III receptor, position 734-740

<400> SEQUENCE: 146

Asp Ala Thr Met Ile Trp Asp
1               5

<210> SEQ ID NO 147
<211> LENGTH: 9
<212> TYPE: PRT
<213> ORGANISM: Artificial sequence
<220> FEATURE:
<223> OTHER INFORMATION: Modified synthetic peptide from rat TGB beta 1
      type III receptor, position 731-739

<400> SEQUENCE: 147

Thr Ser Leu Asp Ala Thr Thr Met Met
1               5

<210> SEQ ID NO 148
<211> LENGTH: 18
<212> TYPE: PRT
<213> ORGANISM: Artificial sequence
<220> FEATURE:
<223> OTHER INFORMATION: Synthetic peptide from rat TGB beta 1 type II
      receptor, position 84-101

<400> SEQUENCE: 148

Cys Val Ala Val Trp Arg Lys Asn Asp Glu Asn Ile Thr Leu Glu Thr
1               5                   10                  15

Val Cys

<210> SEQ ID NO 149
<211> LENGTH: 19
<212> TYPE: PRT
<213> ORGANISM: Artificial sequence
<220> FEATURE:
<223> OTHER INFORMATION: Synthetic peptide from human fetuin, position
      114-132

<400> SEQUENCE: 149

Cys Asp Phe Gln Leu Leu Lys Leu Asp Gly Lys Phe Ser Val Val Tyr
1               5                   10                  15

Ala Lys Cys

<210> SEQ ID NO 150
<211> LENGTH: 19
<212> TYPE: PRT
<213> ORGANISM: Artificial sequence
<220> FEATURE:
<223> OTHER INFORMATION: Synthetic peptide from rat fetuin, position
      114-132

<400> SEQUENCE: 150

Cys Asp Phe His Ile Leu Lys Gln Asp Gly Gln Phe Arg Val Cys His
1               5                   10                  15

Ala Gln Cys
```

```
<210> SEQ ID NO 151
<211> LENGTH: 19
<212> TYPE: PRT
<213> ORGANISM: Artificial sequence
<220> FEATURE:
<223> OTHER INFORMATION: Synthetic peptide from sheep fetuin, position
      114-132

<400> SEQUENCE: 151

Cys Asp Ile His Val Leu Lys Gln Asp Gly Phe Ser Val Leu Phe Thr
1               5                   10                  15

Lys Cys Asp

<210> SEQ ID NO 152
<211> LENGTH: 15
<212> TYPE: PRT
<213> ORGANISM: Artificial sequence
<220> FEATURE:
<223> OTHER INFORMATION: Synthetic peptide from pig endoglin, position
      289-303

<400> SEQUENCE: 152

Val Asn Leu Pro Asp Thr Arg Gln Gly Leu Leu Glu Glu Ala Arg
1               5                   10                  15

<210> SEQ ID NO 153
<211> LENGTH: 15
<212> TYPE: PRT
<213> ORGANISM: Artificial sequence
<220> FEATURE:
<223> OTHER INFORMATION: Synthetic peptide from pig endoglin, position
      481-495

<400> SEQUENCE: 153

Pro Ser Ile Pro Glu Leu Met Thr Gln Leu Asp Ser Cys Gln Leu
1               5                   10                  15

<210> SEQ ID NO 154
<211> LENGTH: 15
<212> TYPE: PRT
<213> ORGANISM: Artificial sequence
<220> FEATURE:
<223> OTHER INFORMATION: Synthetic peptide from pig endoglin, position
      479-493

<400> SEQUENCE: 154

Met Ser Pro Ser Ile Pro Glu Leu Met Thr Gln Leu Asp Ser Cys
1               5                   10                  15

<210> SEQ ID NO 155
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 13-24

<400> SEQUENCE: 155

Leu Leu Leu Leu Val Leu Leu Pro Thr Asp Ala Ser
1               5                   10

<210> SEQ ID NO 156
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 20-31
```

-continued

<400> SEQUENCE: 156

Pro Thr Asp Ala Ser Val Ser Gly Lys Pro Gln Tyr
1               5                   10

<210> SEQ ID NO 157
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 44-55

<400> SEQUENCE: 157

Thr Glu Lys Gly Cys Val Leu Leu Ser Tyr Leu Asn
1               5                   10

<210> SEQ ID NO 158
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 166-177

<400> SEQUENCE: 158

Tyr Ile Gln Asp Pro Lys Gly Asn Arg Ile Ala Gln
1               5                   10

<210> SEQ ID NO 159
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 192-203

<400> SEQUENCE: 159

Phe Pro Leu Ser Ser Glu Pro Phe Gln Gly Ser Tyr
1               5                   10

<210> SEQ ID NO 160
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 247-258

<400> SEQUENCE: 160

Asn Val Ser Val Cys Gly Leu Tyr Thr Tyr Gly Lys
1               5                   10

<210> SEQ ID NO 161
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 248-259

<400> SEQUENCE: 161

Val Ser Val Cys Gly Leu Tyr Thr Tyr Gly Lys Pro
1               5                   10

<210> SEQ ID NO 162
<211> LENGTH: 12

```
<212> TYPE: PRT
<213> ORGANISM: Artificial sequence
<220> FEATURE:
<223> OTHER INFORMATION: Synthetic peptide from human alpha 2
      microglobulin, position 250-261

<400> SEQUENCE: 162

Val Cys Gly Leu Tyr Thr Tyr Gly Lys Pro Val Pro
1               5                   10

<210> SEQ ID NO 163
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 267-278

<400> SEQUENCE: 163

Ser Ile Cys Arg Lys Tyr Ser Asp Ala Ser Asp Cys
1               5                   10

<210> SEQ ID NO 164
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 469-480

<400> SEQUENCE: 164

Pro Cys Gly His Thr Gln Thr Val Gln Ala His Tyr
1               5                   10

<210> SEQ ID NO 165
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 554-565

<400> SEQUENCE: 165

Asp Ser Ala Lys Tyr Asp Val Glu Asn Cys Leu Ala
1               5                   10

<210> SEQ ID NO 166
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 790-801

<400> SEQUENCE: 166

Gln Pro Phe Phe Val Glu Leu Thr Met Pro Tyr Ser
1               5                   10

<210> SEQ ID NO 167
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 827-838

<400> SEQUENCE: 167

Gln Leu Glu Ala Ser Pro Ala Phe Leu Ala Val Pro
```

-continued

<210> SEQ ID NO 168
<211> LENGTH: 12
<212> TYPE: PRT
<213> ORGANISM: Artificial sequence
<220> FEATURE:
<223> OTHER INFORMATION: Synthetic peptide from human alpha 2
      microgobulin, position 825-836

<400> SEQUENCE: 168

Ser Val Gln Leu Glu Ala Ser Pro Ala Phe Leu Ala
1               5                   10

<210> SEQ ID NO 169
<211> LENGTH: 12
<212> TYPE: PRT
<213> ORGANISM: Artificial sequence
<220> FEATURE:
<223> OTHER INFORMATION: Synthetic peptide from human alpha 2
      microgobulin, position 876-887

<400> SEQUENCE: 169

Ala Leu Glu Ser Gln Glu Leu Cys Gly Thr Glu Val
1               5                   10

<210> SEQ ID NO 170
<211> LENGTH: 11
<212> TYPE: PRT
<213> ORGANISM: Artificial sequence
<220> FEATURE:
<223> OTHER INFORMATION: Synthetic peptide from human alpha 2
      microgobulin, position 1001-1012

<400> SEQUENCE: 170

Lys Ser Lys Ile Gly Tyr Leu Asn Thr Gly Tyr
1               5                   10

<210> SEQ ID NO 171
<211> LENGTH: 12
<212> TYPE: PRT
<213> ORGANISM: Artificial sequence
<220> FEATURE:
<223> OTHER INFORMATION: Synthetic peptide from human alpha 2
      microgobulin, position 1005-1016

<400> SEQUENCE: 171

Ile Gly Tyr Leu Asn Thr Gly Tyr Gln Arg Gln Leu
1               5                   10

<210> SEQ ID NO 172
<211> LENGTH: 12
<212> TYPE: PRT
<213> ORGANISM: Artificial sequence
<220> FEATURE:
<223> OTHER INFORMATION: Synthetic peptide from human alpha 2
      microgobulin, position 1162-1173

<400> SEQUENCE: 172

Lys Arg Lys Glu Val Leu Lys Ser Leu Asn Glu Glu
1               5                   10

<210> SEQ ID NO 173
<211> LENGTH: 12
<212> TYPE: PRT
<213> ORGANISM: Artificial sequence
<220> FEATURE:
<223> OTHER INFORMATION: Synthetic peptide from human alpha 2

-continued microglobulin, position 1193-1204

<400> SEQUENCE: 173

Val Gly His Phe Tyr Glu Pro Gln Ala Pro Ser Ala
1               5                   10

<210> SEQ ID NO 174
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 1209-1220

<400> SEQUENCE: 174

Thr Ser Tyr Val Leu Leu Ala Tyr Leu Thr Gln Ala
1               5                   10

<210> SEQ ID NO 175
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 1211-1222

<400> SEQUENCE: 175

Tyr Val Leu Leu Ala Tyr Leu Thr Ala Gln Pro Ala
1               5                   10

<210> SEQ ID NO 176
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 1256-1267

<400> SEQUENCE: 176

Val Ala Leu His Ala Leu Ser Lys Tyr Gly Ala Ala
1               5                   10

<210> SEQ ID NO 177
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 1232-1243

<400> SEQUENCE: 177

Tyr Gly Arg Asn Gln Gly Asn Thr Trp Leu Thr Ala
1               5                   10

<210> SEQ ID NO 178
<211> LENGTH: 12
<212> TYPE: PRT
<213> ORGANISM: Artificial sequence
<220> FEATURE:
<223> OTHER INFORMATION: Synthetic peptide from human alpha 2
      microglobulin, position 1234-1245

<400> SEQUENCE: 178

Arg Asn Gln Gly Asn Thr Trp Leu Thr Ala Phe Val
1               5                   10

TGFβ1 INHIBITOR PEPTIDES

FIELD OF THE INVENTION

This application pertains to peptides that have antagonistic activity in preventing TGFβ1 from interacting with TGFβ1 receptors.

Cell growth is regulated by various proteins of the growth factor group (Schalch D S et al. (1979) Endocrinology 104:1143–1151). The most important growth factors involved in cell development, and able to act by autocrine and paracrine mechanisms, include the transforming growth factors (TGFs) (Braun L. et al. (1988) Cell Biol. 85:1539–1543; Lyons R M and Moses H L (1990) Eur. J. Biochem. 187:467–473).

The term TGF was first used for describing the activity produced by a cell line transformed with the murine sarcoma virus (deLarco J E and Todaro G J (1978) Proc. Natl. Acad. Sci. 75:4001–4005; Mizel S B et al. (1980) Proc. Natl. Acad. Sci. 77:2205–2208). The supernatant of these cells was able to induce normal growth, in soft agar, of cells that require a solid support for growth. More specific studies demonstrated two classes of TGF, called TGFα and TGFβ, which in turn comprise families of related proteins. The TGFβ family consists of 5 isoforms (Brand T. and Schneider M D (1995) J. Mol. Cell Cardiol. 27:5–18) of dimeric structure (Schlunneger M P and Grutter M G (1992) Nature 358:430–434; Brand T. and Schneider M D (1995) J. Mol. Cell Cardiol. 27:5–18). Investigations of the mature proteins, purified from a single species, demonstrated a high degree of identity between their sequences (Table 1).

Table 1. Homology among different types of TGFβs. TGFβ1, TGFβ2 and TGFβ3 derived from humans, TGFβ4 derived from chicken and TGFβ5 from frog. (Roberts A B and Sporn M B, 1990).

| | % of | | | | |
|---|---|---|---|---|---|
| | TGFβ1 | TGFβ2 | TGFβ3 | TGFβ4 | TGFβ5 |
| TGFβ1 | 100 | | | | |
| TGFβ2 | 71 | 100 | | | |
| TGFβ3 | 72 | 76 | 100 | | |
| TGFβ4 | 82 | 64 | 71 | 100 | |
| TGFβ5 | 76 | 66 | 69 | 72 | 100 |

TGFβ1 is synthesized as a precursor of 390 amino acids called Pre-Pro-TGFβ1. In a first hydrolysis there is release of a hydrophobic fragment of 29 amino acids, which gives rise to Pro-TGFβ1. Then the mature TGFβ1 is released by another cut in a region that precedes the terminal amino of TGFβ1 and that consists of two arginines, giving rise to a protein of 112 amino acids with a molecular weight of 12 kDa. To produce the biologically active form, two of these monomers join together by means of disulphide bridges, yielding a dimer of 25 kDa. Alterations of this structure cause loss of biological function (Barnard J A et al. (1990) Biochim. Biophys. Acta 1032:79–87).

Various domains are known to exist within the structure of TGFβ1. One of these domains is found to be located between amino acids 40 and 82 and is involved in the binding of TGFβ1 to its cell receptors (Quian S W et al. (1992) Proc. Natl. Acad. Sci. 89:6290–6294; Burmester J K et al. (1993) Proc. Natl. Acad. Sci. 90:8628–8632).

Receptors of TGFβ1 and Other Binding Proteins

Five types of specific receptors for TGFβ1 have been characterized (Cheifetz S et al. (1988) J. Biol. Chem. 263:17225–17228 and López Casillas F. et al. (1991) Cell 67:785–795). These receptors have different affinities for the different types of TGFβ1. Receptors of type I, II ard III are the best understood so far (reviewed in Attisano L et al. (1994) Biochim. Biophys. Acta 1222:71–80; Derynck R. (1994) Trends Biochem. Sci. 19:548–553; Yingling et al. (1995) Biochim. Biophys. Acta 1242:115–136). Type IV receptors have also been described (MacKay K. and Danielpour D. (1991) J. Biol. Chem. 266:9907–9911) and type V (Ichijo H. et al. (1991) J. Biol. Chem. 266:22459–22464). It has also been reported that the transmembrane and cytoplasmic domains of endoglin (Cheifetz S at al. (1993) J. Biol. Chem. 267:19027–19030; Bellón T. et al. (1993) Eur. J. Immunol. 23:2340–2345; Yamashita et al. (1995) J. Biol. Chem. 269:1995–2001; Zhang H. et al. (1996) J. Immunol. 156:564–573)) have approximately 70% similarity with the type III receptors, both human and of the rat.

RIII would be the one with the task of binding TGFβ1 and presenting it to RII which in its turn would form a complex with RI (Yamashita et al. (1994) J. Biol. Chem. 269: 20172–2017B) ox to complexes in which various molecules of RI are combined with RII (Weiss G. and MassaguéJ. (1996) EMBO J. 15:276–289). RII-RI interaction would give rise to phosphorylation of RI and subsequent activation of its serine/threonine kinase which would phosphorylate to second messengers like the MADR2 proteins (Macias-Silva M et al., (1996) Cell 87:1215–1224).

(1)

Role of TGFβ1 in Hepatic Differentiation and Regeneration

The effects produced are different depending on the moment of development and on the type of cell.

Enlargement of the extracellular matrix, on acting upon the liver stellate cells (Ito cells), the principal source of matrix proteins (Mustce T A et al. (1987) Science 237:1333–1336).

Differentiation of the epithelial cells and hepatocytes (Florini J R et al. (1986) J. Biol. Chem. 261:16509–16513).

Inhibition of cell growth during the process of liver regeneration. This effect is of great importance in the maintenance of cell rest in vivo (Kato Y et al. (1988) Proc. Natl. Acad. Sci. 85:9552–9556).

Inhibition of endocytosis of the receptor of the epithelial growth factor (EGF) as has been observed in cultures of foetal rat hepatocytes (Noda M. and Rodan G A (1987) J. Cell Physiol. 133:426–437).

Role of TGFβ1 in Hepatic Fibrosis

TGFβ1 has been found to be associated with the processes of hepatic fibrosis (Czaja M J et al. (1989) J. Cell Biol. 108:2477–2482; Annoni G. et al. (1992) J. Hepatol. 14:259–264) causing an increase in production of proteins of the extracellular matrix, by the liver stellate cells (lipocytes or Ito cells), of their receptors and inhibiting synthesis of the proteolytic enzymes that degrade the matrix (Ignotz R A and Massagué J. (1986) J. Biol. Chem. 261:4337–4345). In the liver, TGFβ1 induces the synthesis of collagen and fibronectin in the liver stellate cells (Weiner F R (1990) Hepatology 11:111–117). There is also auto-regulation by increasing its own synthesis, via induction of its mRNA.

TGFβ1 has also been found to be involved in increased synthesis of α2-macroglobulin synthesized by the hepatocytes and the activated liver stellate cells. By binding to TGFβ1 and causing its inactivation (Bachem M G (1994) Ann NY Acad. Sci. 737:421–424), (α2-macroglobulin is said to eliminate TGFβ1 from the extracellular compartments.

Investigation of patients with chronic liver damage has shown that there is a correlation between expression of TGFβ1 and expression of the mRNA for the type I procollagen and the serum levels of type III peptide of procollagen (Castilla A. et al. (1991) N. Engl. J. Med. 324:933–940).

Patients with cirrhosis of the liver have a shorter than normal life expectancy owing to the complications that arise in the course of the disease, such as portal hypertension or hepatic failure.

Effect of TGFβ1 on the Extracellular Matrix

Interaction of TGFβ1 with the cell receptors causes:

Activation of synthesis of procollagen, fibronectin (Ignotz R A et al. (1987) J. Biol. Chem. 262:6443–6446) and related proteins, including membrane proteins capable of interacting with the components of the extracellular matrix (Carter W G (1982) J. Biol. Chem. 257:13805–13815).

Inhibition of the synthesis of proteolytic enzymes capable of degrading the matrix (Fukamizu H. and Grinnell F. (1990) Exp. Cell Res. 190:276–282).

Stimulation of the synthesis of inhibitors of proteolytic enzymes (Fukamizu H. and Grinnell F. (1990) Exp. Cell Res. 190:276–282).

These effects lead to an increase in interactions of the cell with the extracellular matrix, which combined with greater reorganization of the proteins of which it is composed, gives rise to an increase in the total quantity of extracellular matrix (Roberts C J et al. (1988) J. Biol. Chem. 263:4586–4592). These findings confirm that TGFβ1 is involved in cicatrization processes (Fukamizu H. and Grinnell F. (1990) Exp. Cell Res. 190:276–282; Barnard J A et al. (1990) Biochim. Biophys. Acta 1032:79–87).

Peptides as Inhibitors of Ligand-Receptor Interaction

There is the possibility of using small molecules, synthetic peptides, as analogues of molecules that are present in the body, with the aim of emulating their function. Studies conducted by LeSateur et al. demonstrate the possibility of using cyclized analogues of nerve growth factor (NGF), emulating the β turn region, permitting its binding to the receptor (LeSateur L. et al. (1996) Nature Biotechnology 14:1120–1122). It is also possible to use peptides as antagonists of these molecules, preventing the native factor interacting with its receptor by blocking mediated by the peptide (Lasarte J J et al. (1994) J. Acquired Immune Deficiency Syndromes 7:129–134; LeSateur et al. (1995) J. Biol. Chem. 270:6564–6569). Earlier studies had demonstrated the usefulness of synthetic peptides as inhibitors of ligand-receptor interaction even when the recognition epitope is not continuous (Daniels A J et al. (1995) Mol. Pharmacol. 48:425–432). Other studies conducted with the type II receptor of TGFβ1 and with fetuin, a glycoprotein in the group of type II receptors, have demonstrated the possibility of using cyclized peptides as inhibitors of the interaction of TGFβ1 with RII (Demetriou M. et al. (1996) J. Biol. Chem. 271:12755–12761). With this cyclization it becomes possible to obtain peptides with a structure similar to that which could be obtained in vivo.

SUMMARY OF INVENTION

Peptides that are antagonists of the binding of TGFβ1 to its receptors in the body. The peptides are characterized in that they have partial amino acid sequences that are identical or similar to those of TGFβ1 itself and/or its receptors.

DETAILED DESCRIPTION

Figure 1:
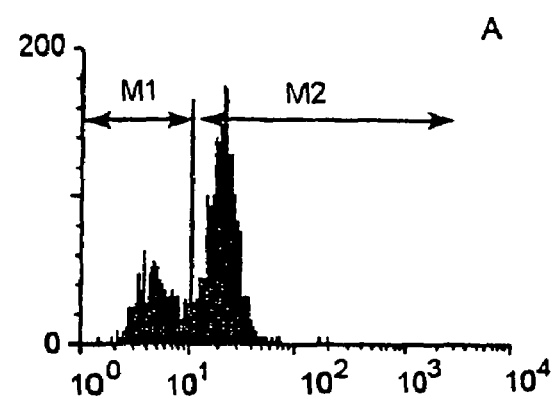
FIG. 1. Inhibition of binding of TGFβ1 to the MV-1-Lu cells by peptide P144, measured by flow cytometry. A, image obtained on examining the cells incubated with biotinylated TGFβ1 and developed with avidin-FITC. B, image obtained on examining the cells incubated with avidin-FITC without prior addition of TGFβ1. C, image obtained on examining the cells incubated with TGFβ1 previously incubated with peptide P144 at a concentration of 0.42 μg/μl, and developed with avidin-FITC. The fluorescence emitted is shown on the abscissa, while the ordinate shows the number of cells for each value of fluorescence. The fields corresponding to the cells labelled with TGFβ1-biotin and avidin-FITC (M2) and to the unlabelled cells (M1) are also shown.
Figure 1:
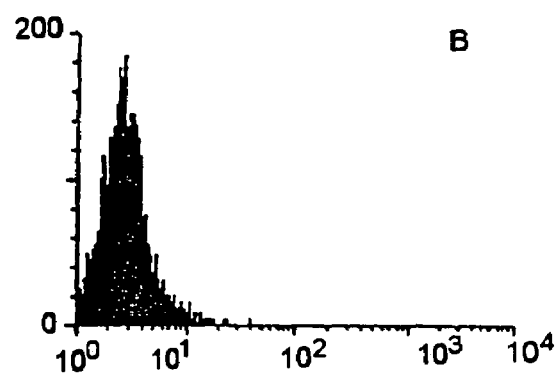
Figure 1:
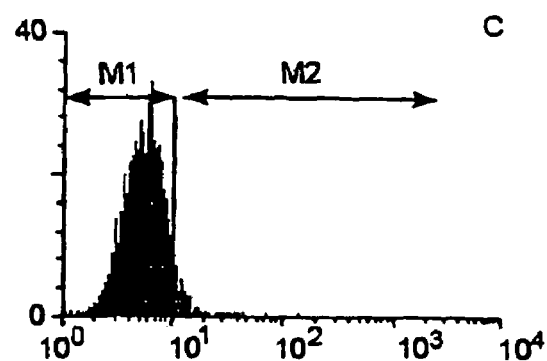

For the reasons stated above, we consider that peptides derived both from TGFβ1 and from its receptors, or from proteins with capacity for binding to TGFβ1, could be inhibitors of the action of TGFβ1. We therefore decided to explore this possibility.

Selection of the Peptides to be Synthesized

The peptides for synthesis were selected in different ways depending on whether they were derived from TGFβ1 or from its receptors.

In the case of the sequence of TGFβ1, peptides were synthesized from 15 amino acids that include the whole sequence of TGFβ1. Each peptide had 10 amino acids in common with its two immediate neighbours.

In the case of the sequences of its receptors, the peptides were chosen on the basis of software designed in our laboratory. One of the computer programs compares two amino acid sequences, with the aim of predicting partially complementary regions. Other programs were also used that were able to predict the regions of the proteins that would be most exposed, on the basis of the hydrophobicity and hydrophilicity of the amino acids making up their sequence.

Synthesis of Peptides

The peptides were synthesized by the solid phase method (Merrifield (1963) J. Am. Chem. Soc. 85: 2149–54), using fluorenylmethyloxycarbonyl (Fmoc) as a temporary protecting group of the alpha-amino group (Atherton et al. (1989) Journal of Chemical Society Perkins Transactions 1: 538–546). For the synthesis of small quantities of a large number of peptides, a multiple synthesizer was used, permitting the simultaneous synthesis of 96 peptides (Borrás-Cuesta et al. (1991) Biologicals 19: 187–190). The peptides were stored at −80° C. in the solid state until used.

Purification of the Peptides by HPLC

The synthesized peptides were analysed and purified by high-performance liquid chromatography (HPLC), using a Waters 600E-900 system (Millipore Corp., Bedford, USA).

A Waters Radial-Pak™ C$_{18}$ 300 Å 15 μm, 8×100 mm column (Millipore Corp., Bedford, USA) was used for analysis of the peptides by analytical HPLC. The peptide was dissolved in a 0.1% solution of TFA in distilled water, to a maximum concentration of 1 mg/ml. The solution of peptide was injected (100 μl) into the column and was eluted in a water/acetonitrile gradient (FIG. 15) (Romil Ltd., Cambridge, USA) both with 0.1% TFA at a flow rate of 1 ml/min. The fractions that contained the peptide were detected by its absorbance at 220 nm and 280 nm (photodiode array detector, Waters 991, Millipore Corp., Bedford, USA).

A Waters Delta-Pak™ C$_{18}$ 300 Å 15 μm, 25×100 mm column (Millipore Corp., Bedford, USA) was used for its purification. The peptide was dissolved and was injected (2 ml) under the same conditions as in the preceding case, employing the same gradient at a flow rate of 5 ml/min. The fraction that contained the pure peptide was collected in a flask.

In Vitro Tests. Investigation of the Activity of the Peptides

Cell Lines

A line derived from mink pulmonary epithelium, V-1-Lu, was used (CCL-64, American Type Cell Culture, Virginia, USA). The cells were grown in 162 cm$^2$ culture flasks (Costar Corporation, Cambridge, USA) in a stove at 37° C. and 5% CO$_2$, until subconfluence was attained. A complete medium was used: RPMI 1640 with L-glutamine (Gibco-BRL, Life Technologies Ltd., Paisley, Scotland) supplemented with 5% of foetal calf serum (FCS, Biological Industries, Kibbutz Beit Haemek, Israel), 10 mM HEPES (1M HEPES Buffer, Bio-Whittaker, Verviers, Belgium) and antibiotics (100 U/ml penicillin and 100 μg/ml streptomycin).

Test of Inhibition of the Growth of the MV-1-Lu Cell Line

The MV-1-Lu cells grown as indicated above were removed from the bottom of the culture flasks using 5 ml of trypsin-EDTA (Biological Industries, Kibbutz Beit Haemek, Israel), resuspended in complete medium and centrifuged at 1500 rev/min for 8 minutes. After centrifugation the cells were resuspended in complete medium to a concentration of 50,000 cells/ml. For conducting the test, 10 ml of the cell suspension were taken and dispensed in 96-well, flat-bottom culture plates (Costar Corporation, Cambridge, USA), adding 100 μl/well, and were incubated overnight at 37° C. and 5% CO$_2$, which permits adhesion of the cells to the bottom of the wells. At the end of this time, the peptides to be tested were added in RPMI, to a final concentration of 200 μg/ml in the presence of a concentration of 200 pg/ml of TGFβ1 in RPMI (R&D Systems Europe Ltd., Abingdon, UK). The final concentration of FCS in the well was 2.5%. After 24 hours of incubation, 1 μCi of tritiated thymidine was added per well (25 Ci/mmol [methyl-$^3$H]-thymidine, Amersham Life Science, Buckinghamshire, U K) with incubation for a further 12 hours (Grubeck-Loebenstein B. et al. (1989) J. Clin. Invest. 83:764–770; Brennan F M et al. (1990) Clin. Exp. Immunol. 81:278–285).

At the end of the incubation periods the cells were removed from the bottom of the wells with trypsin-EDTA and were collected using a manual harvester (Titertek cell harvester, Skatron Instruments Inc., Sterling, USA) which ruptures the cells, collecting the DNA in nitrocellulose filters (Filter MAT 11731, Skatron Instruments Inc., Sterling, USA) where it is fixed. The filters were placed individually in 5 ml polypropylene tubes to which 4 ml of scintillation fluid was added (Biogreen-11, Reactivos Scharlau S. A., Barcelona, Spain). The activity of each tube was quantified for 90 seconds in a β LKB scintillation counter (Beta plate system, LKB, Uppsala, Sweden).

Investigation of Inhibition of Binding of TGFβ1 to the Cell Receptors

Selective Labelling of the Cell Receptors (Affinity Labelling)

The MV-1-Lu cells were removed from the culture flasks incubating them at 37° C. for 10 minutes, with 10 ml of solution 1 (128 mM NaCl, 5 mM KCl, 25 mM 4-(2-hydroxyethyl)-1-piperazine ethanesulphonate at pH 7.5, 5 mM glucose and 1 mM EDTA). The cells thus removed were resuspended in solution 2 (128 Mm NaCl, 5 mM KCl, 50 mM 4-(2-hydroxyethyl)-1-piperazine ethanesulphonate at pH 7.5, 1.2 mM $CaCl_2$, 1.2 mM $MgSO_4$ and 5 mg/ml BSA) and were collected by centrifugation at 1000×g for 5 minutes. After centrifugation the cells were resuspended in solution 2 at a concentration of $10^6$ cells/ml.

From this cell suspension, 0.5 ml aliquots were made in 24-well plates (Greiner GmbH, Frickenhausen, Germany), the peptides were added, in 50 μl of a 0.8 mg/ml solution, then this was incubated for 2 hours at 4° C. with stirring. Next, $^{125}$I-TGFβ1 (2 μCi) was added to a final concentration of 277.2 pM ($^{125}$I-TGFβ1 human recombinant 800–2200 Ci/mmol, Amersham Life Science, Buckinghamshire, UK) and this was incubated for a further two hours at 4° C. with stirring.

After incubation, the cells were transferred to a centrifuge tube and were centrifuged cold at 12,000×g for 1 minute. They were then washed twice in cold solution 2 and were resuspended in 0.5 ml of cold solution 2, 5 μl of dimethyl sulphoxide (DMSO 99.5%, Sigma Chemical Co., St. Louis, USA) and disuccimidyl suberate (DSS, Pierce Chemical Co., Rockford, USA) giving a final concentration of 0.25 mM of DSS. Reaction was stopped at 15 minutes by dilution, centrifugation and washing with a solution containing 0.25M saccharose, 10 mM Tris and 1 mM EDTA at pH 7.4. The precipitate of cells was resuspended in 0.5 ml of Triton X-100 (Bio-Rad Laboratories, Hercules, USA) 1% v/v, 10 mM Tris at pH 7.0, 1 mM EDTA, 0.1 mM phenylmethylsulphonyl fluoride, 1 μg/ml pepstatin and 1 μg/ml leupeptin (Sigma Chemical Co., St. Louis, USA) and incubated for 40 minutes at 4° C. The fraction that is insoluble in detergent is separated by centrifugation at 12,000×g for 15 minutes. The fractions that are soluble in detergent (supernatant) and insoluble (precipitate) were frozen at −20° C. (Massagué J. and Like B. (1985) J. Biol. Chem. 260: 2636–2645).

Electrophoresis of Proteins in Sodium Polyacrylamide Dodecyl Sulphate Gel

The fractions soluble and insoluble in detergent were used for analysis by electrophoresis in acrylamide/bisacrylamide gels at 7.5% for 5–6 hours at 220 volts.

The proteins were stained with a solution of (comassie brillant blue® R250 (Serva Feinbiochemica GmbH, Heidelberg, Germany) in methanol (50%), acetic acid (10%) and distilled water, for 30 minutes. Subsequent washings were effected with a solution of methanol (50%), acetic acid (10%) and distilled water for 15 minutes, in the first washing, and methanol (2.5%), acetic acid (0.5%) and distilled water, in the subsequent washings, until the background colour was removed.

Flow Cytometry

Inhibition of the binding of TGFβ1, mediated by peptides, to the cell receptors was measured by the direct immunofluorescence method. An immunofluorescence kit was used for this (Fluorokine rh TGFβ1-biotin, R&D Systems Europe Ltd., Abingdon, U K). This test is based on the capacity of biotinylated TGFβ1 to bind to the cell receptors, in a specific manner, and the subsequent interaction of the biotin with fluorescein-labelled avidin, so that the signal intensity will depend on the quantity of TGFβ1 bound to the cell receptors.

The MV-1-Lu cells grown in 162 $cm^2$ flasks were removed using solution 1 (described previously) and were resuspended in physiological saline for centrifugation at 500×g for 5 minutes. After centrifugation, the cells were resuspended again in physiological saline at a concentration of $4 \times 10^6$ cells/ml. 25 μl of the cell suspension was added to 12×75 mm borosilicate tubes, to which was added the peptide to be tested in 40 μl of RPMI 1640 medium, giving a final concentration of 0.42 μg/μl and 10 μl of biotinylated TGFβ1. As a control of specificity, 10 μl of a biotinylated reagent supplied with the kit was added, 10 μl of biotinylated TGFβ1 was added as a positive control and 20 μl of anti-TGFβ1 blocking antibody was added as a negative control. Physiological saline was added to all the controls until a total volume of 75 μl was reached. All the tubes were incubated for 1 hour at 4° C. in darkness.

Figure 16:
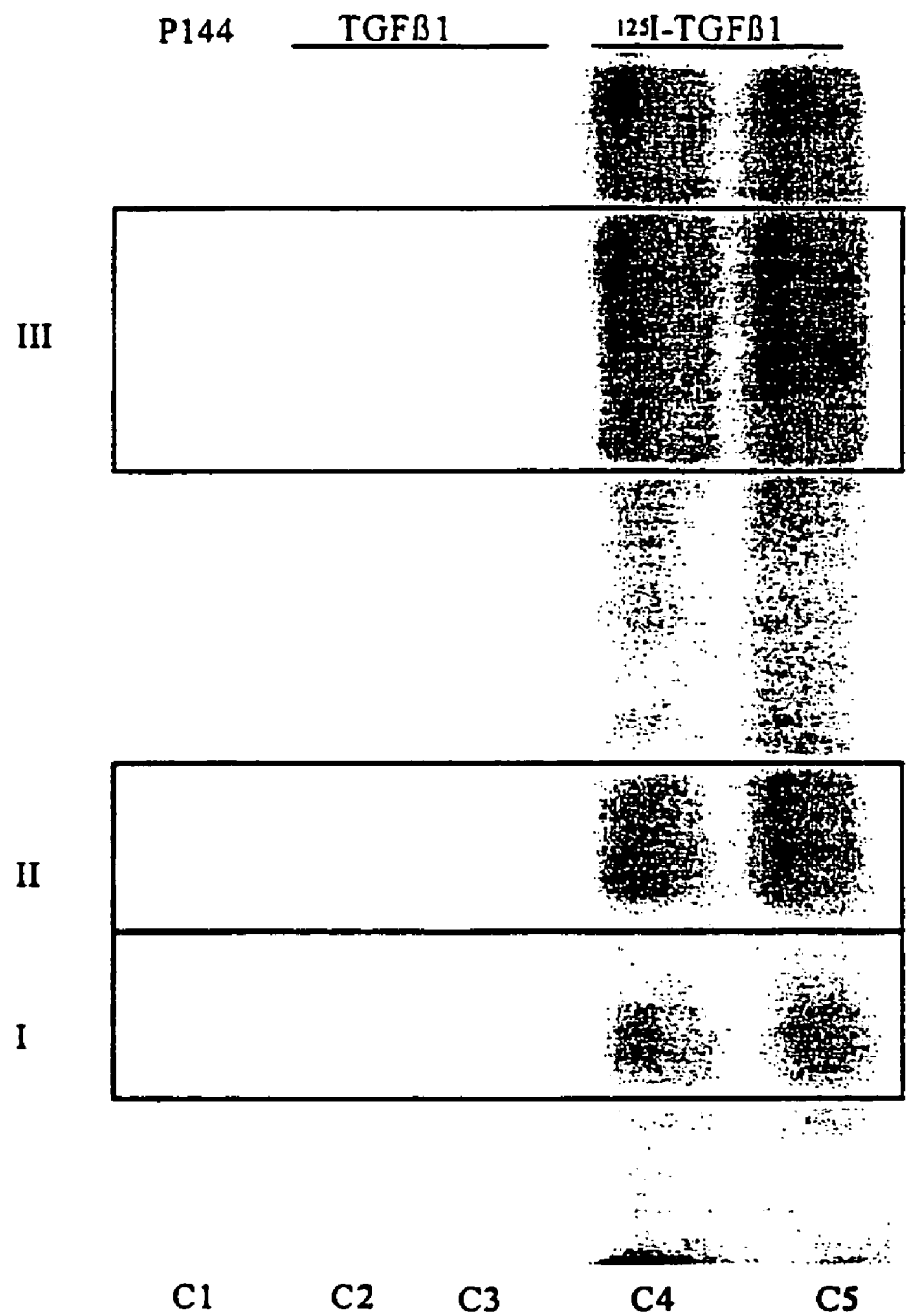
FIG. 16. Autoradiograph of an affinity labelling test of the receptors of TGFβ1. Lane C1: preincubation was effected with peptide P144 at a concentration $10^6$ times greater than the molar concentration of $^{125}$I-TGFβ1. Lanes C2 and C3: effect of preincubation of the cells with a concentration of non-radioactive TGFβ1 10 times greater than that of $^{125}$I-TGFβ1 (negative control): Lanes C4 and C5: effect of incubation of the cells with a concentration of 0.1 μM of $^{125}$I-TGFβ1 that corresponds to an activity of 0.2 μCi (positive control). It can be seen that there is inhibition of the binding of $^{25}$I-TGFβ1 to the cell receptors both by peptide P144 and by the non-radioactive TGFβ1.

At the end of the incubation period, 10 μl of fluorescein-labelled avidin was added, incubating for 30 minutes at 4° C. in darkness, after which 2 ml of a washing solution (RDF1) was added, followed by centrifugation at 500×g for 6 minutes. The cell precipitate was resuspended in 0.2 ml of cold PBS for cytometry (FACScan, Becton Dickinson Immunocytometry Systems, California, USA). This method permits measurement of the fluorescence emitted by each cell when a laser beam is incident upon it, by means of a computer program (Lisys™ II, Becton Dickinson Immunocytometry Systems, California, USA). FIG. 16 shows a typical image from analysis by flow cytometry.

To obtain the data on inhibition of the binding of TGFβ1 to the receptors, the positive control of the test was used for delimiting the fields corresponding to the labelled cells, that have bound to the TGFβ1-biotin (M2) and to the unlabelled cells (M1). Once the fields had been delimited, the percentage of cells located in each of them was calculated. The same was done with the data obtained when the peptide was incubated with TGFβ1-biotin or with the cells, depending on whether they were derived from the receptors or the TGFβ1 respectively. With these data, the percentage inhibition of each peptide was calculated using the following formula: 100−((M2 Peptide-M2 Negative)×100/(M2 Positive-M2 Negative)).

Experiments In Vivo. Experimental Model of Fibrosis

Male white rats (albino Wistar strain) from simultaneous litters (5 weeks±1.5 weeks) were used, in order to obtain a group that was homogeneous in age and initial weight. Throughout the experiments, the animals were kept in conditions of constant temperature (22° C.) with a 12-hour cycle of light and darkness. They had free access to water and food.

Figure 2:
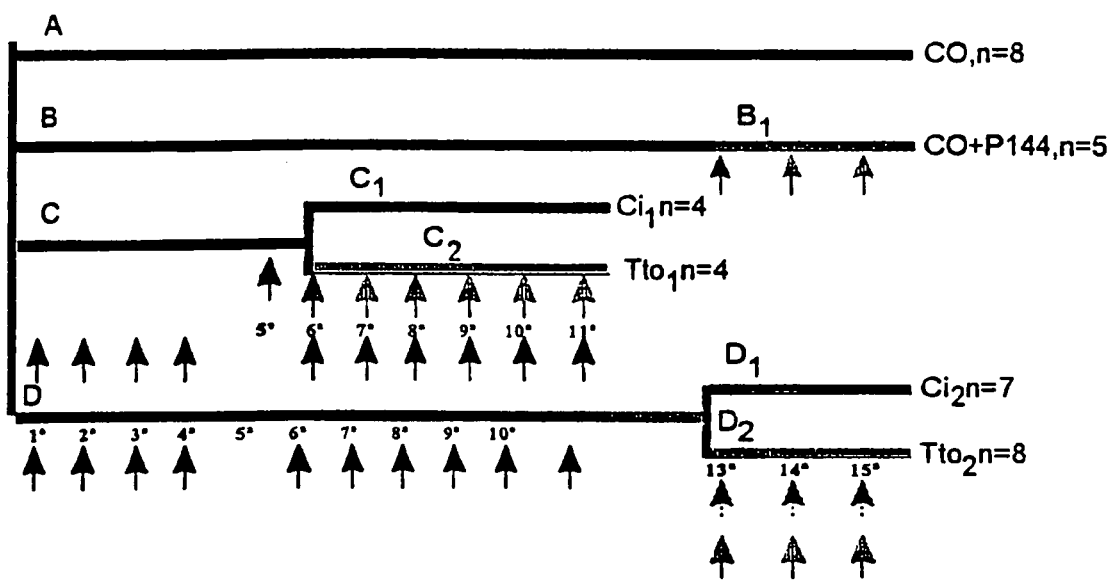
FIG. 2. Schematic representation of the process of cirrhosis by $CCl_4$. Black arrows indicate when two weekly doses of $CCl_4$ were administered to the rats, and black dashed arrows show when there was one weekly dose. The grey arrows indicate administration of peptide P144. A: Healthy controls; B: Healthy controls+P144, $B_1$: with peptide 70 μg/day; C: Cirrhotic; $C_1$ with saline; $C_2$ with peptide 70 μg/day; D: Cirrhotic with $CCl_4$+phenobarbital; $D_1$ plus saline; $D_2$ plus peptide 70 μg/day.

Hepatic cirrhosis (HC) was induced by inhalation of carbon tetrachloride for 11 weeks, twice per week (López Novoa J M et al. (1976) Patologia IX:223–240; Camps J. et al. (1987) Gastroenterology 93:498–505). Exposure to $CCl_4$ was effected by bubbling compressed air, at a flow rate of 3 liters/min, through a gas wash-bottle. One minute of exposure was used initially, increasing by one minute per week until 4 minutes was reached in the fourth week. $CCl_4$ was not administered during the fifth week, starting again at the sixth week with an exposure of 5 minutes. This exposure time was maintained until week 11. 400 mg/l of phenobarbital (Luminal®, Bayer, Leverkusen, Germany) was added to the drinking water, from one week before starting exposure to $CCl_4$ and until the end of the experimental period. Before starting the treatment, one week was left, in which they were not administered $CCl_4$. During treatment they were administered a weekly dose of $CCl_4$, as recorded (FIG. 2).

Distribution of the Animals

The animals were divided into 4 groups before beginning the process of induction of hepatic cirrhosis.

Healthy controls (Co): Animals that were not subjected to the fibrosis process.

Treated healthy controls (Co+P144): Animals that were not subjected to the fibrosis process and that were administered the peptide P144 during the last 3 weeks (coinciding in time with the treatment of the group of rats $Tto_2$).

Cirrhotic controls 1 ($Ci_1$): Animals subjected to the process of induction of cirrhosis by inhalation of $CCl_4$ twice per week. These animals were separated into 2 groups on reaching the fifth week:

Cirrhotic controls 1 ($Ci_1$): Animals that continued to be subjected to the process of induction of fibrosis up to week 11, without being administered the peptide P144. They were administered saline serum on alternate days, throughout the induction process (weeks 5 to 11).

Treated cirrhotics 1 ($Tto_1$): Animals that were administered the peptide P144 derived from the sequence of the type III receptor, on alternate days, during the process of induction of fibrosis, from week 5 to week 11.

Cirrhotic controls 2 ($Ci_2$): Animals that continued to be subjected to the process of induction of fibrosis without receiving the peptide P144 or saline serum. This group was subdivided into another two on reaching week 11.

Cirrhotic controls 2 ($Ci_2$): Cirrhotic animals that were not subjected to any type of treatment, kept as controls. These animals received injections of saline serum for 3 weeks (weeks 13 to 15).

Treated cirrhotics 2 ($Tto_2$): Cirrhotic animals that were treated with the peptide derived from the sequence of the type III receptor (P144), for 3 weeks (weeks 13 to 15).

Treatment of the animals

Group $Tto_1$: These animals underwent treatment during the fibrosis process. Treatment with the peptide started in the fifth week (before exposure to $CCl_4$ for 5 minutes) and continued up to the end of the eleven weeks of the cirrhosis induction process.

Group $Tto_2$: These animals underwent treatment after completion of the process of induction of cirrhosis (11 weeks). Treatment started one week after the last inhalation of $CCl_4$ and continued for 21 days.

Before starting the treatment and on its completion, blood was taken from all the animals that had been treated with the peptide. The peptide was administered by subcutaneous injection in the abdominal zone at a dose of 70 µg/animal in 500 µl of physiological saline.

Sacrifice of the Animals and Dissection of the Liver

On completion of treatment of the animals with the peptide, both in the model with rats and in that with mice, the animals were sacrificed by decapitation, after taking blood from them from the retro-orbital plexus with a capillary.

This was followed immediately by dissection of the liver and collection of samples.

The samples were cut and placed in formol as fixing solution, for later histologic examination. Other fragments were placed in cryotubes, which were immersed in liquid nitrogen and then stored at −80° C.

Anatomopathologic Evaluation of the Liver

Histologic examination was carried out on fragments of liver previously fixed in formol for at least 24 hours, after which they were placed in ethanol (70%).

After dehydrating they were embedded in paraffin blocks. Successive sections 3 µm thick were prepared from the blocks obtained, using a Leitz rotary microtome and steel blades. Prior to staining the sections were deparaffined in xylene (AnalaR, BDH, Poole, UK) for 15 minutes, after heating them at 60° C. in a stove for 15 minutes, and they were hydrated by successive passes through alcohols of decreasing concentration 100%, 96%, 80% and 70% and finally in water. The following stains were used:

Haematoxylin-eosin.

Masson's trichromic (Locquin M. and Langeron, (1985) in Manual de Microscopia Ed. Labor S. A. Barcelona): Uses a specific dye for collagen proteins (green light).

Sirius Red: A stain specific for collagen.

Confirmation of Hepatic Fibrosis: Image Analysis

For image analysis of the samples obtained, a light microscope was used (Olympus BH-2, Tokyo, Japan) connected to a video camera (Sony DXP-950P, Sony Co., Tokyo, Japan), with which the various fields of each preparation were photographed. Six fields were taken at random from each preparation stained with Sirius Red. The various images captured were analysed by means of a computer program (Visilog 4.1.5, Noesis, Orsay, France) which calculates the area of fibrosis and the total area of the preparation. From these data, a fibrosis index (area of fibrosis/total area) was calculated for each field. To be able to use this program it was necessary to modify image acquisition by using polarized light filters (Olympus U-POT, Tokyo, Japan) and green light filters (Olympus IF550, Tokyo, Japan) which made it possible to automate the process of sample analysis.

Detection of Collagen in 14 µm Sections of Paraffin-Treated Tissue

The 14 µm sections that were used for this technique were obtained in the same way as the 3 µm sections mentioned previously. These sections were subjected to a process of deparaffination for 12 hours in xylene. Once the paraffin had been eliminated, the samples were hydrated by passing them through different grades of alcohol 96%, 80%, 50%, completing the process in distilled water.

Once hydrated, they were subjected to a process of prestaining in a solution of 160 mg of Fast Green FCF (Fluka Chemika-BioChemika, Buchs, Switzerland) in 160 ml of saturated picric acid (Merck, Darmstadt, Germany) for 15 minutes in darkness. The samples were washed by immersion in water until they no longer coloured the wash water. Once the surplus dye was removed, the samples were stained for 30 minutes in darkness in a solution of 160 mg of Direct Red 80 (Fluka Chemika-BioChemika Buchs, Switzerland) and 64 mg of Fast Green, both dyes in 160 ml of saturated picric acid. They were washed again until the surplus dye was removed, and then the samples were removed from the slides by scraping the sample off with a small spatula. The sections removed in this way were placed in separate tubes containing 3 ml of a solution of NaOH 0.1 N (Quimó n, Montplet&Esteban S. A., Barcelona, Spain) and methanol (1:1). Aliquots were taken from the various tubes for reading in the spectrophotometer (Lambda 2 UV/VIS spectrophotometer, Perkin-Elmer, Norwalk, USA) at wavelengths of 540 nm and 630 nm using as blank an aliquot of the solution of NaOH 0.1 N and methanol (López de León A. and Rojkind (1985) Histochem. Cytochem. 33:737–743; Gaudio E. et al. (1993) Int. J. Exp. Path. 74:463–469).

In accordance with the works of Gaudio E. et al. (1993) Int. J. Exp. Path. 74:463–469), the following formulae were used for finding the quantities of collagen and total protein:

$$\text{mg collagen} = \frac{\text{absorbance at 540 nm} - \text{absorbance at 630 nm}}{37}$$

$$\text{mg collagen/mg total protein} = \frac{\text{mg collagen}}{\text{mg collagen} + \text{mg non-collagen proteins}}$$

$$\text{Non-collagen proteins} = \frac{\text{absorbance at 630 nm}}{3}$$

Statistical Analysis of the Results

The data obtained in the experiments in vivo were subjected to statistical analysis. Normality of the quantitative variables was verified by the Shapiro-Wilks test.

As the data had not been adjusted to a normal distribution, non-parametric statistical analysis was undertaken. Comparison between groups was effected by means of Kruskal-Wallis H followed by comparison of Mann-Whitney U. The data were presented graphically by means of boxes, with representation of the median of the data (thick line inside each box), together with the interquartile range (height of the box), whereas the "whiskers" of each box represent the highest and lowest observations within a given interquartile range.

The association between variables was investigated using Fisher's exact test. Logistic regression was employed for investigating the independence of association of these variables.

A value of P equal to or less than 0.05 was regarded as significant.

All the statistical analyses were accomplished using the program SPSS for Windows V 6.1.3.

Inhibition In Vitro of the Activity of TGFβ1

Test of Inhibition of Cell Growth of the MV-1-Lu Line

Figure 3:
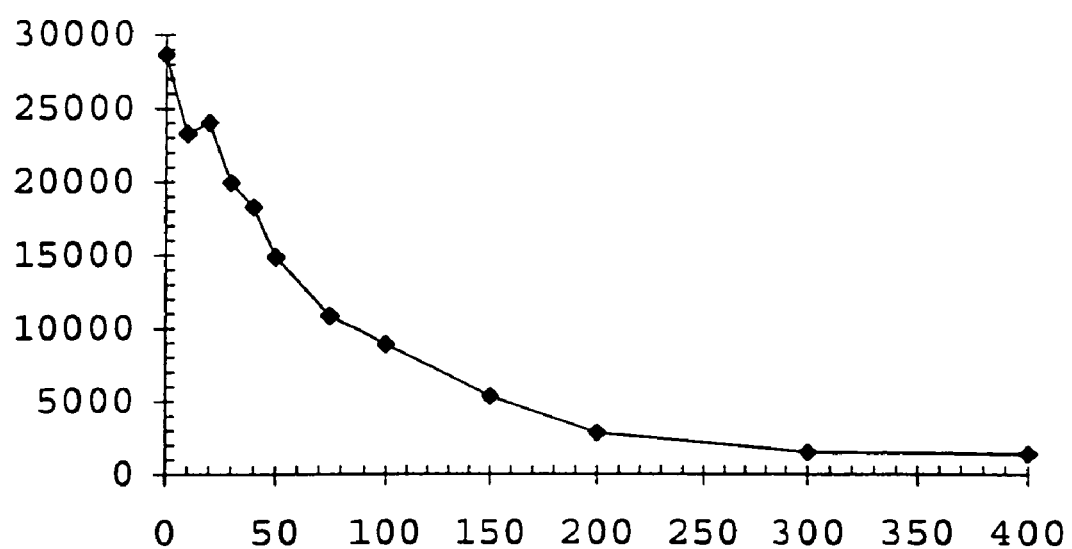
FIG. 3. Effect of TGFβ1 on growth of MV-1-Lu cells. The cells are cultivated at a density of 5000 cells/well at the concentrations of TGFβ1 indicated, pg/ml Abscissa: TGFβ1 concentration (pg/ml); Ordinate: c.p.m.

TGFβ1 is a cytokine that is able to inhibit the growth in vitro of the MV-1-Lu cell line (Grubeck-Loebenstein B. et al. (1989) J. Clin. Invest. 83:764–770; Brennan F M et al. (1990) Clin. Exp. Immunol. 81:278–285), therefore this line was used for testing the blocking effect of peptides on TGFβ1. After different combinations of media, cells and thymidine, we studied the effect of different concentrations of TGFβ1 on incorporation of [methyl-$^3$H]thymidine by MV-1-Lu cells in culture, for determining the most suitable conditions for the test. These conditions are shown in FIG. 3.

Once both the optimum concentration of MV-1-Lu cells (5000 cells/well) and the lowest concentration of TGFβ1 capable of producing inhibition of about 90% (200 pg/ml, FIG. 18) had been determined, the inhibitory effect of the synthetic peptides at a concentration of 200 μg/ml was tested.

Inhibition In Vitro of the Activity of TGFβ1 by Synthetic Peptides

The synthetic peptides that are potentially inhibitors of TGFβ1 activity, selected as indicated above in the section: selection of the peptides to be synthesized (both those derived from proteins that bind to TGFβ1 and TGFβ1 itself) were tested using the MV-1-Lu cell line. The peptides were dissolved in buffered RPMI medium, free from foetal calf serum, and the following procedure was used:

The peptides belonging to the sequence of the receptor, or complementary to the peaks of hydrophilicity of TGFβ1, were incubated for 30 minutes in the presence of this cytokine and were then combined with the cell culture. The peptides derived from the sequence of TGFβ1 were added to the cell culture prior to addition of TGFβ1, since they interact with the receptors of the cell surface. These incubations were effected in 100 μl of the same medium as was used for adding the cells. The active peptides permitted cell growth to a greater or lesser degree depending on its ability to inhibit TGFβ1.

Inhibition of TGFβ1 by Means of Peptides Derived from TGFβ1

In a first stage, overlapping peptides derived from TGFβ1 were synthesized. These peptides (Table 2) were synthesized in the hope that some of them could bind to the cell receptors, thus preventing the binding of natural TGFβ1 to these receptors.

Table 2. Peptides derived from TGFβ1. The number of the peptide is shown, together with its position in the complete sequence, as well as its amino acid sequence. For convenience of synthesis, all the peptides were synthesized with an alanine added at the C-terminal end which is not shown in the table.

| Peptide | Sequence | | |
|---|---|---|---|
| P1$_{(280-293)}$ | AlaLeuAspThrAsnTyrCysPheSerSerThrGluLysAsn | SEQ ID NO: | 11 |
| P2$_{(284-297)}$ | AsnTyrCysSerSerThrGluLysAsnCysCysValArg | SEQ ID NO: | 12 |
| P3$_{(288-301)}$ | SerSerThrGluLysAsnCysCysValArgGlnLeuTyrIle | SEQ ID NO: | 13 |
| P4$_{(294-307)}$ | CysCysValArgGlnLeuTyrIleAspPheArgLysAspLeu | SEQ ID NO: | 14 |
| P5$_{(298-311)}$ | GlnLeuTyrIleAspPheArgLysAspLeuGlyTrpLysTrp | SEQ ID NO: | 15 |
| P6$_{(302-315)}$ | AspPheArgLysAspLeuGlyTrpLysTrpIleHisGluPro | SEQ ID NO: | 16 |
| P7$_{(306-319)}$ | AspLeuGlyTrpLysTrpIleHisGluProLysGlyTyrHis | SEQ ID NO: | 17 |
| P8$_{(308-321)}$ | GlyTrpLysTrpIleHisGluProLysGlyTyrHisAlaAsn | SEQ ID NO: | 18 |
| P9$_{(312-325)}$ | IleHisGluProLysGlyTyrHisAlaAsnPheCysLeuGly | SEQ ID NO: | 19 |
| P10$_{(316-329)}$ | LysGlyTyrHisAlaAsnPheCysLeuGlyProCysProTyr | SEQ ID NO: | 20 |
| P11$_{(319-333)}$ | HisAlaAsnPheCysLeuGlyProCysProTyrIleTrpSerLeu | SEQ ID NO: | 1 |
| P12$_{(322-335)}$ | PheCysLeuGlyProCysProTyrIleTrpSerLeuAspThr | SEQ ID NO: | 2 |
| P13$_{(326-339)}$ | ProCysProTyrIleTrpSerLeuAspThrGlnTyrSerLys | SEQ ID NO: | 21 |
| P14$_{(330-343)}$ | IleTrpSerLeuAspThrGlnTyrSerLysValLeuAlaLeu | SEQ ID NO: | 22 |

-continued

| Peptide | Sequence | | | |
|---|---|---|---|---|
| P15(335-349) | ThrGlnTyrSerLysValLeuAlaLeuTyrAsnGlnHisAsnPro | SEQ | ID | NO: 23 |
| P16(336-349) | GlnTyrSerLysValLeuAlaLeuTyrAsnGlnHisAsnPro | SEQ | ID | NO: 24 |
| P17(340-353) | ValLeuAlaLeuTyrAsnGlnHisAsnProGlyAlaSerAla | SEQ | ID | NO: 25 |
| P18(343-358) | LeuTyrAsnGlnHisAsnProGlyAlaSerAlaAlaProCysCys | SEQ | ID | NO: 26 |
| P19(344-358) | TyrAsnGlnHisAsnProGlyAlaSerAlaAlaProCysCys | SEQ | ID | NO: 27 |
| P20(348-360) | AsnProGlyAlaSerAlaAlaProCysCysValProGln | SEQ | ID | NO: 28 |
| P21(350-363) | GlyAlaSerAlaAlaProCysCysValProGlnAlaLeuGlu | SEQ | ID | NO: 29 |
| P22(354-367) | AlaProCysCysValProGlnAlaLeuGluProLeuProIle | SEQ | ID | NO: 30 |
| P23(358-371) | ValProGlnAlaLeuGluProLeuProIleValTyrTyrVal | SEQ | ID | NO: 31 |
| P24(364-377) | ProLeuProIleValTyrTyrValGlyArgLysProLysVal | SEQ | ID | NO: 32 |
| P25(368-381) | ValTyrTyrValGlyArgLysProLysValGluGlnLeuSer | SEQ | ID | NO: 33 |
| P26(372-385) | GlyArgLysProLysValGluGlnLeuSerAsnMetIleVal | SEQ | ID | NO: 34 |
| P27(378-391) | GluGlnLeuSerAsnMetIleValArgSerCysLysCysSer | SEQ | ID | NO: 35 |

Figure 4:
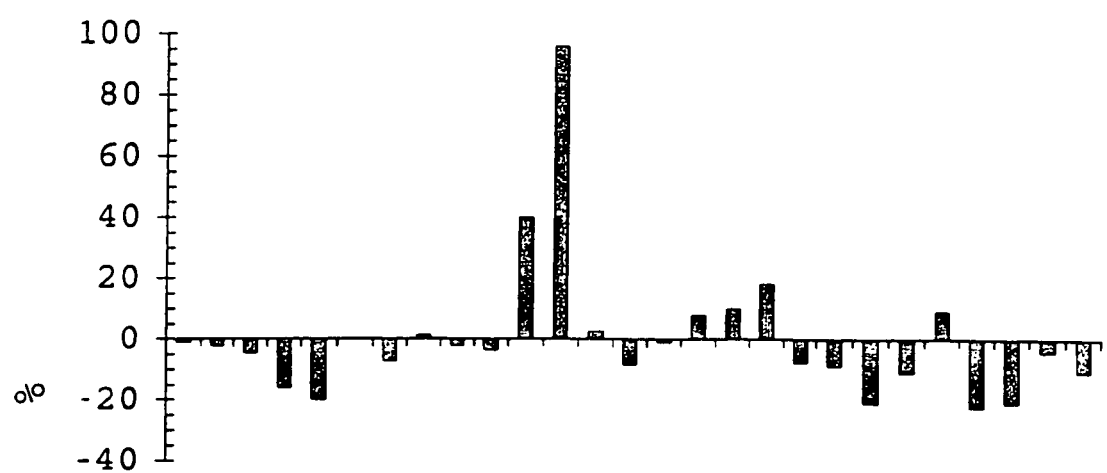
FIG. 4. Percentage inhibition of TGFβ1 (200 pg/ml) by peptides from TGFβ1. All the peptides were tested at a concentration of 200 μg/ml. Inhibition of TGFβ1 of 100% corresponds to the growth of MV-1-Lu cells that is obtained in the absence of TGFβ1.
Figure 5:
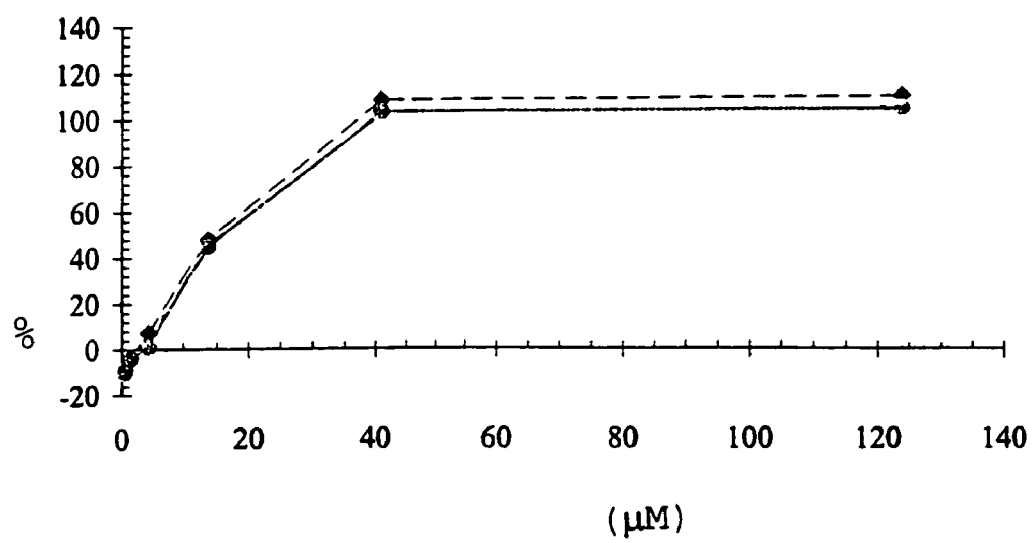
FIG. 5. Percentage inhibition of the activity of TGFβ1 (200 pg/ml) in the presence of various nominal concentrations of peptide P12, filtered (◆) and unfiltered (●).
Figure 6:
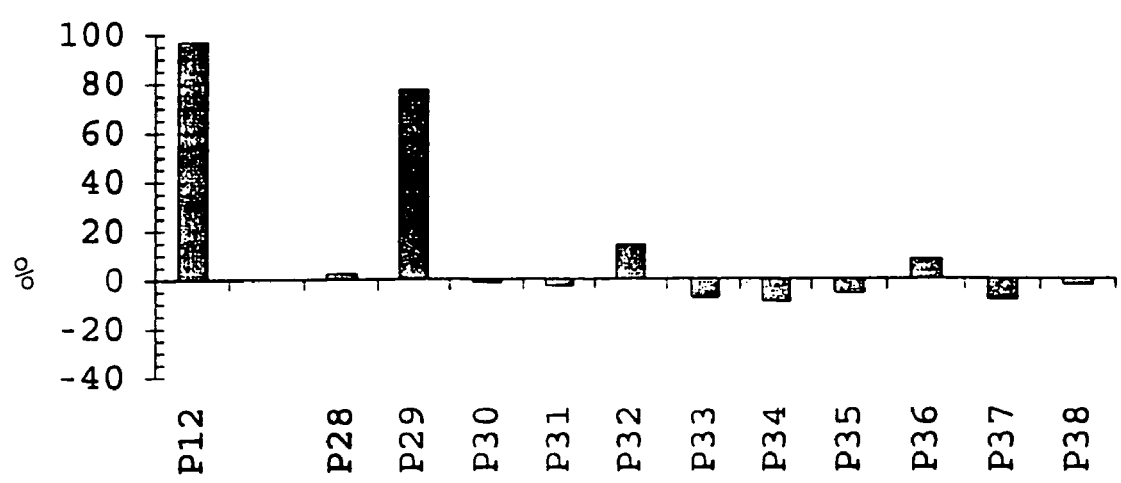
FIG. 6. Percentage inhibition of TGFβ1 (200 pg/ml) by peptides from TGFβ1. All the peptides were tested at a concentration of 200 μg/ml. Inhibition of TGFβ1 of 100% corresponds to the growth of MV-1-Lu cells that is obtained in the absence of TGFβ1.

FIG. 4 shows the inhibitory effect of the peptides in Table 6 on the activity of TGFβ1. Since TGFβ1 inhibits growth of the MV-1-Lu cells, inhibition of this cytokine by the peptides leads to re-establishment of growth of the MV-1-Lu cells.

Figure 7:
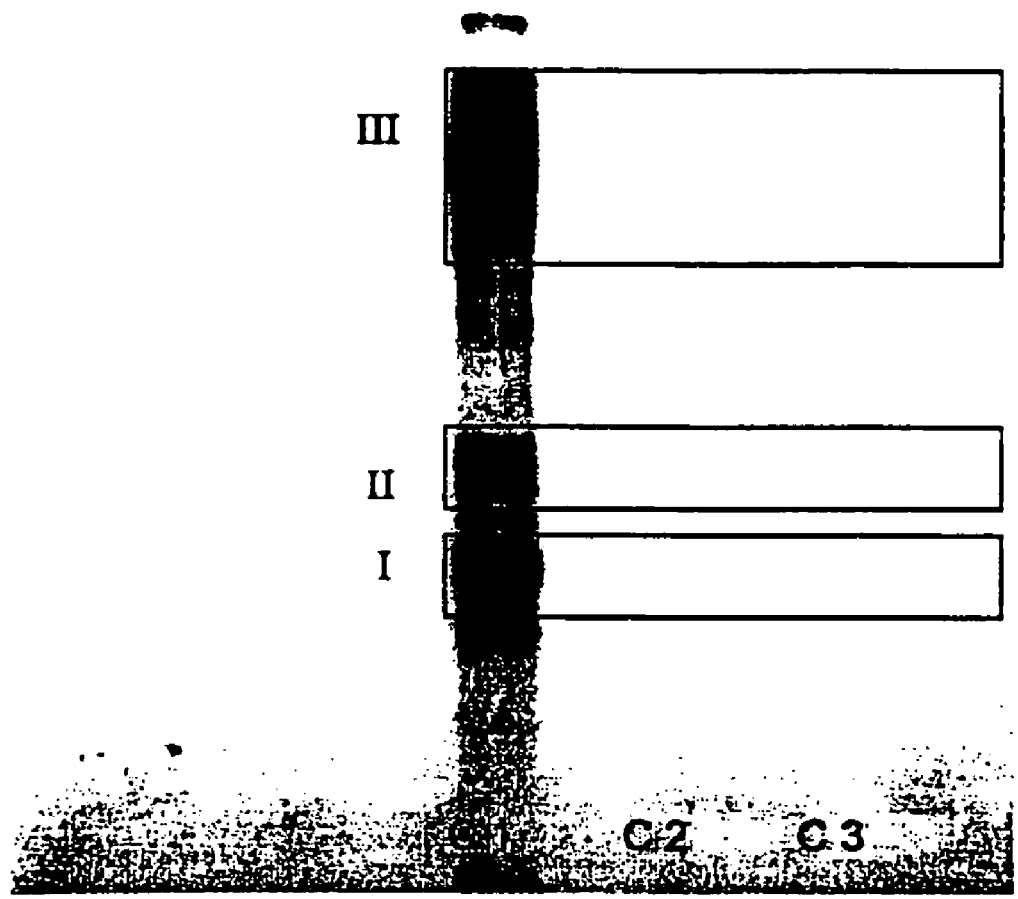
FIG. 7. Autoradiograph of an affinity labelling test of the receptors of TGFβ1. Lane C1: effect of incubation of the cells with a concentration of 0.16 μM of $^{125}$I-TGFβ1 which corresponds to an activity of 0.3 μCi (positive control). Lane C2: effect of preincubation of the cells with a concentration of non-radioactive TGFβ110 times greater than that of $^{125}$I-TGFβ1 (negative control). Lane C3: preincubation was effected with peptide P29 at a concentration $10^6$ times greater than the molar concentration of $^{125}$I-TGFβ1. It can be seen that there is inhibition of the binding of $^{125}$I-TGFβ1 to the type I, II and III cell receptors both by peptide P29 and by non-radioactive TGFβ1.
Figure 8:
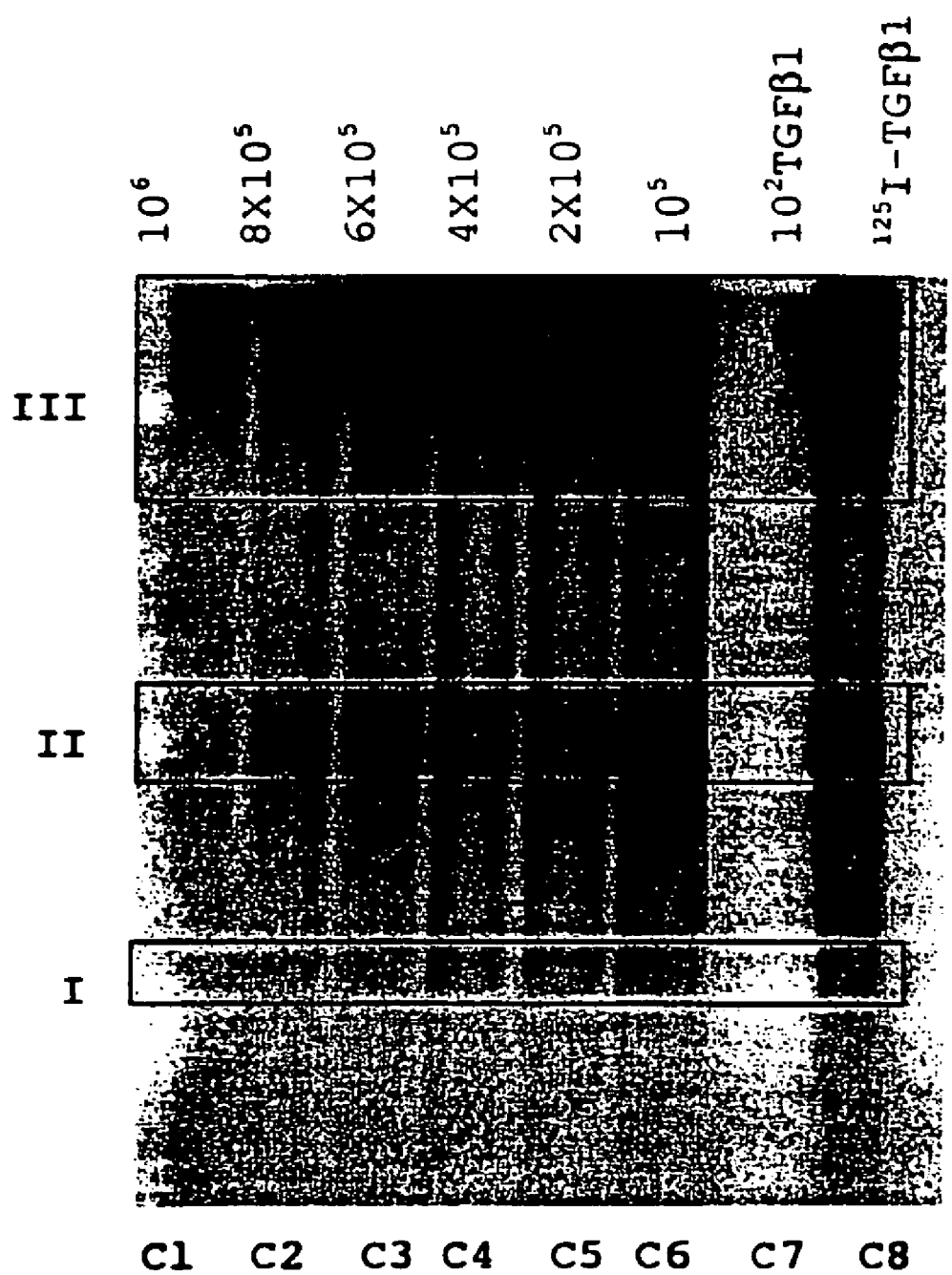
FIG. 8. Autoradiograph of an affinity labelling test of the receptors of TGFβ1. Lanes C1 to C6: effect of preincubation of the MV-1-Lu cells, with different concentrations of peptide P29 ($10^6$, $8\times10^5$, $6\times10^5$, $4\times10^5$, $2\times10^5$ and $10^5$ times the molar concentration of $^{125}$I-TGFβ1 respectively), prior to addition of $^{125}$I-TGFβ1. Lane C7: effect of preincubation of the MV-1-Lu cells with unlabelled TGFβ1 ($10^2$ times the molar concentration of $^{125}$I-TGFβ1) prior to addition of $^{125}$I-TGFβ1 (negative control). Lane C8: effect of incubation of the MV-1-Lu cells with a concentration of 0.42 μM of $^{125}$I-TGFβ1, corresponding to an activity of 0.4 μCi, without prior preincubation (positive control).
Figure 9:
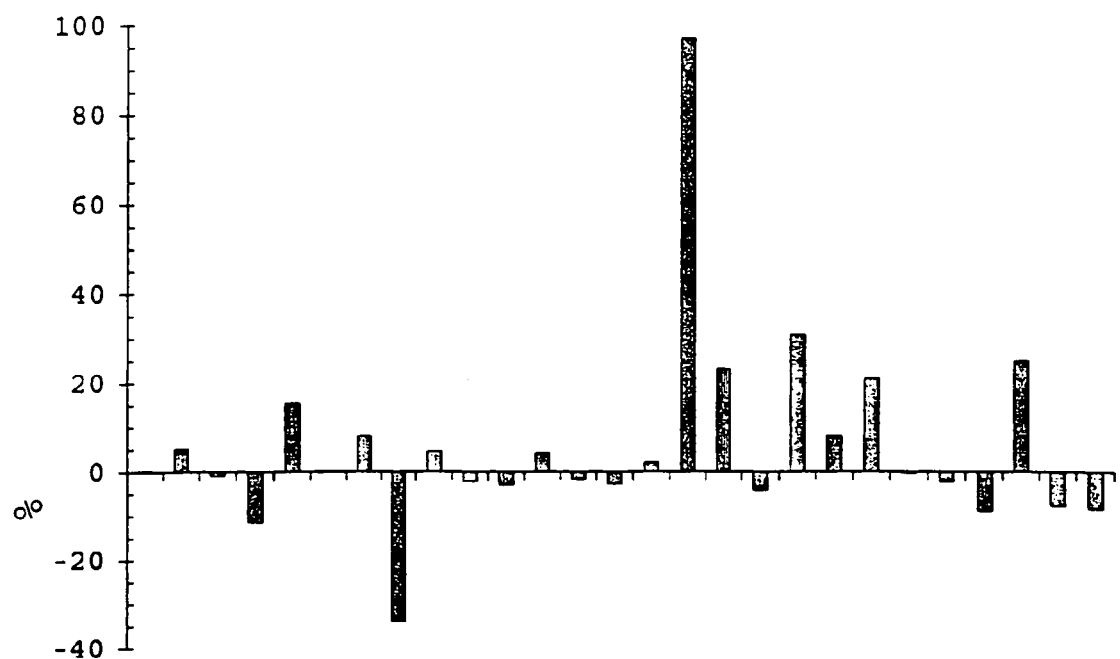
FIG. 9. Percentage inhibition of TGFβ1 (200 pg/ml) by receptor peptides predicted as complementary to regions of TGFβ1. All the peptides were tested at a concentration of 200 μg/ml. Inhibition of TGFβ1 of 100% corresponds to the growth of MV-1-Lu cells that is obtained in the absence of TGFβ1.
Figure 10:
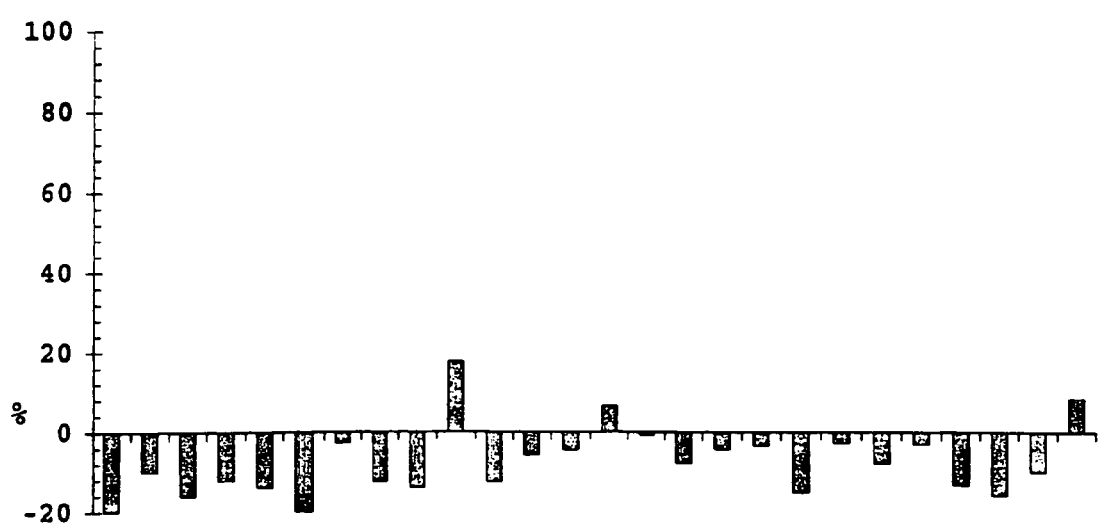
FIG. 10. Percentage inhibition of TGFβ1 (200 pg/ml) by overlapping peptides derived from the extracellular region of the type III receptor. All the peptides were tested at a concentration of 200 μg/ml. Inhibition of TGFβ1 of 100% corresponds to the growth of MV-1-Lu cells that is obtained in the absence of TGFβ1.
Figure 11:
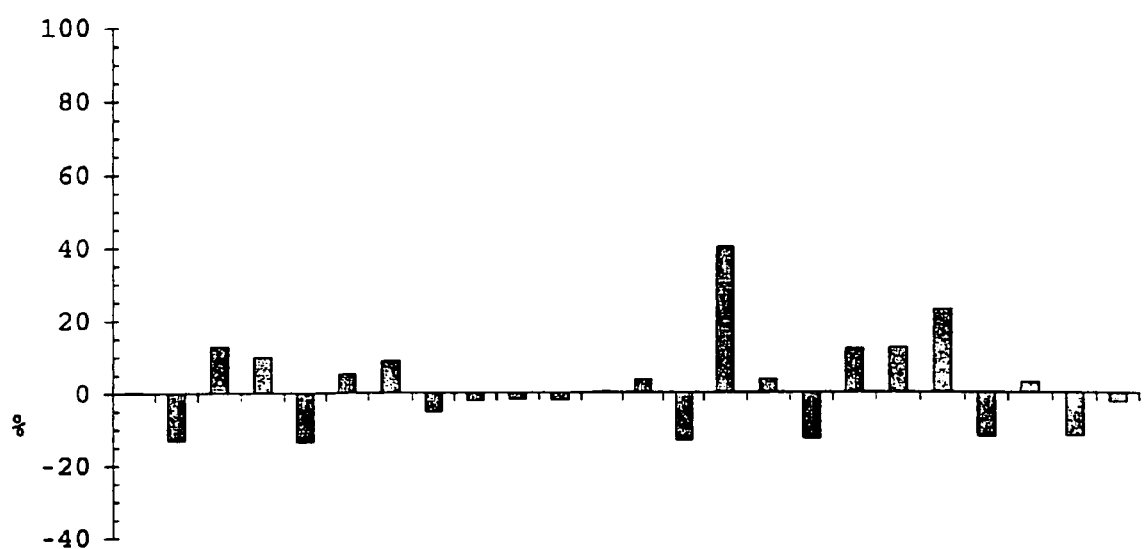
FIG. 11. Percentage inhibition of TGFβ1 (200 pg/ml) by overlapping peptides derived from the extracellular region of the type III receptor. All the peptides were tested at a concentration of 200 μg/ml. Inhibition of TGFβ1 of 100% corresponds to the growth of MV-1-Lu cells that is obtained in the absence of TGFβ1.
Figure 12:
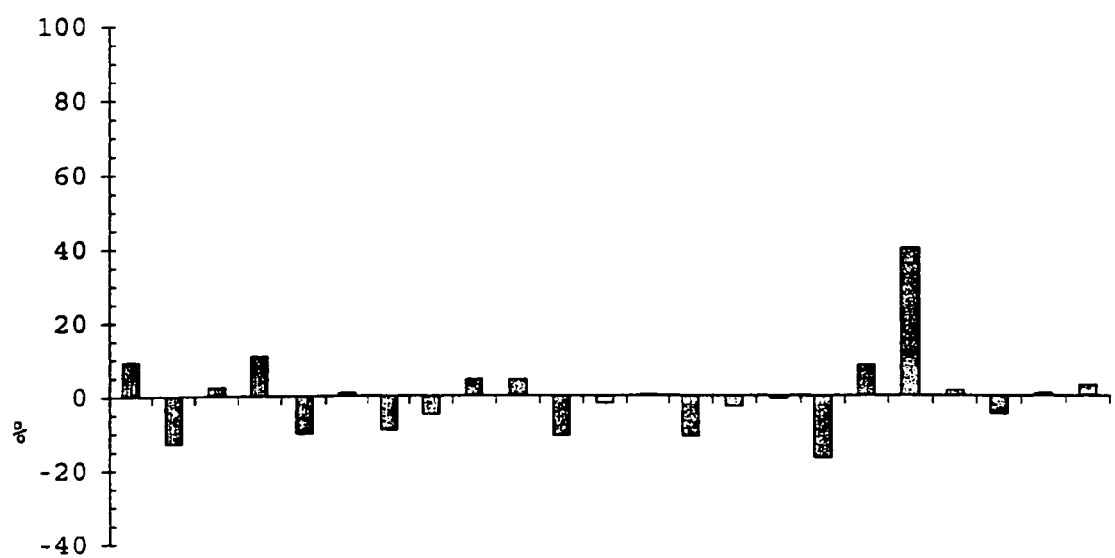
FIG. 12. Percentage inhibition of TGFβ1 (200 pg/ml) by Overlapping peptides derived from the extracellular region of the type III receptor. All the peptides were tested at a concentration of 200 μg/ml. Inhibition of TGFβ1 of 100% corresponds to the growth of MV-1-Lu cells that is obtained in the absence of TGFβ1.

As can be seen from FIG. 4, the peptide P12, derived from the sequence of TGFβ1, is the one that exhibits greater inhibitory activity of TGFβ1. For more detailed investigation of the inhibitory effect of peptide P12, an investigation was conducted into the effect of the concentration of the peptide on inhibition of the cytokine, which is described below.

Dose-Response Test of the Inhibition of TGFβ1 by the Peptide P12

The effect of the concentration of peptide P12 on inhibition of the activity of TGFβ1 was investigated. As this peptide was not readily soluble in the test medium, stock solutions or suspensions were prepared with a nominal concentration of peptide (that which would have been achieved if the peptide had dissolved completely) and aliquots were taken from these, and were filtered or even were used directly for the inhibition tests.

FIG. 5 examines the inhibitory effect of nominal concentrations of peptide, before and after filtration. It can be seen that peptide P12, with and without filtration, has practically the same activity.

Once the results had been obtained with peptide P12, it was decided to lengthen the peptide, both in the N-terminal and the C-terminal direction, and to investigate the effect on its activity. In addition, changes were made to its sequence to improve its solubility and study the importance of the two cysteines in its sequence on the inhibitory activity of TGFβ1. The peptides synthesized are stated in Table 3.

Table 3. Peptides derived from modification of peptide P12.

| Peptide | Sequence | |
|---|---|---|
| $P12_{(322-335)}$ | PheCysLeuGlyProCysProTyrIleTrpSerLeuAspThr | SEQ ID NO: 2 |
| $P28_{(322-344)}$ | PheCysLeuGlyProCysProTyrIleTrpSerLeuAspThrGlnLysVal LeuAlaLeuTyr | SEQ ID NO: 36 |
| $P29_{(333-335)}$ | HisGluProLysGlyTyrHisAlaAsnPheCysLeuGlyProCysProTyr IleTrpSerLeuAspThr | SEQ ID NO: 10 |
| P30 | PheSerLeuGlyProCysProTyrIleTrpSerLeuAspThr | SEQ ID NO: 37 |
| P31 | PheCysLeuGlyProSerProTyrIleTrpSerLeuAspThr | SEQ ID NO: 38 |
| P32 | PheSerLeuGlyProSerProTyrIleTrpSerLeuAspThr | SEQ ID NO: 39 |
| P33 | PheCysLeuGlyProCysProTyrIleTrpSerAspAspAsp | SEQ ID NO: 40 |
| P34 | AspAspAspGlyProCysProTyrIleTrpSerLeuAspThr | SEQ ID NO: 41 |
| P35 | AspAspAspGlyProCysProTyrIleTrpSerAspAspAsp | SEQ ID NO: 42 |
| P36 | GlyProCysProTyrIleTrpSerAspAspAsp | SEQ ID NO: 43 |
| P37 | AspAspAspGlyProCysProTyrIleTrpSer | SEQ ID NO: 44 |
| P38 | AspGlyProCysProTyrIleTrpSerAsp | SEQ ID NO: 45 |

FIG. 6 shows the results of inhibition of TGFβ1 by the peptides in Table 3.

It can be seen from FIG. 6 that peptide P29 is active. This peptide includes the previously tested peptide P12 and has 9 extra amino acids towards the N-terminal end (FIG. 4). Investigations conducted by Quian S W et al. (1992) Proc. Natl. Acad. Sci. 89:6290–6294) and by Burmester J K et al. (1993) Proc. Natl. Acad. Sci. 90:8628–8632) using chimeric recombinant proteins identified a region of TGFβ1 that is necessary for the activity of this cytokine (amino acids 40 to 82 in the sequence of mature TGFβ1). It was speculated that peptide P29 (amino acids 34 to 56 in the sequence of mature TGFβ1), extending over a larger region than peptide P12 (amino acids 43 to 56), might acquire a three-dimensional structure more like the structure of the TGFβ1 in circulation. For this reason, peptide P29 was used for tests of binding to the cell receptors, based on affinity labelling.

Tests of Inhibition of the Binding of TGFβ1 to its Receptors by Peptide P29 (Affinity Labelling)

Peptide P29, derived from the sequence of TGFβ1, was used in affinity labelling tests for verifying its capacity for inhibition of the binding of TGFβ1 to its cell receptors (Material and Methods).

Owing to the different activity of the batches of $^{125}I$-TGFβ1 employed, the concentrations of peptide used in the tests were adjusted according to the concentration of the $^{125}$I-TGFβ1 batch used in each case. The results of these tests are shown in FIGS. 7 and 8.

Further tests were carried out to find the minimum concentration required for blocking the binding of $^{125}$I-TGFβ1 to the cell receptors.

Inhibition of TGFβ1 by Peptides Derived from the Sequence of the Type III Receptor of the Rat With the aim of finding new peptides that are inhibitors of the activity of TGFβ1, peptides derived from the type III receptor of the rat were synthesized. Some peptides were chosen on the basis of regions of their sequence that were predicted as complementary to blocks of amino acids of the sequence of TGFβ1. It was hoped that these peptides would be capable of binding to free TGFβ1, sequestering it and preventing its binding to the cell receptors.

Other peptides were synthesized by overlapping 10 amino acids and covering part of the extracellular region of the type III receptor (amino acids 45 to 410). It has been described that a soluble type III receptor exists that corresponds to the extracellular region of the receptor, this region is cut from the membrane and acts as a sequestrator of the TGFβ1 in circulation (López Casillas F. et al. (1991) Cell 67:785–795). Later studies described two possible regions of binding to TGFβ1, one of which is located at the N-terminal end of the receptor (López-Casillas et al. (1994) J. Cell Biol. 124: 557–568) and the other is located in the region closest to the membrane, towards the C-terminal end (Fukushima D. et al. (1993) J. Biol. Chem. 268:22710–22715; Pepin M C et al. (1995) FEBS Lett 377:368–372). For these reasons peptides of the extracellular region of this receptor were synthesized, on the supposition that these peptides might be capable of sequestering the circulating TGFβ1.

The peptides synthesized are shown in Table 4.

Table 4. Peptides derived from the type III receptor of the rat. The number of the peptide and its sequence are shown. P39 to P65 are peptides predicted as complementary to TGFβ1 and P66 to P138 are overlapping peptides covering the extracellular region of the receptor. For convenience of synthesis, all the peptides were synthesized with an alanine added at the C-terminal end which is not shown in the table.

| Peptide | Sequence | | |
|---|---|---|---|
| P39$_{(91–102)}$ | AsnProIleAlaSerValHisThrHisHisLysPro | SEQ ID NO: | 46 |
| P40$_{(104–115)}$ | ValPheLeuLeuAsnSerProGlnProLeuValTrp | SEQ ID NO: | 47 |
| P41$_{(109–120)}$ | SerProGlnProLeuValTrpHisLeuLysThrGlu | SEQ ID NO: | 48 |
| P42$_{(110–121)}$ | ProGlnProLeuValTrpHisLeuLysThrGluArg | SEQ ID NO: | 49 |
| P43$_{(333–344)}$ | TrpAlaLeuAspAsnGlyTyrArgProValThrSer | SEQ ID NO: | 50 |
| P44$_{(428–439)}$ | ProIleValProSerValGlnLeuLeuProAspHis | SEQ ID NO: | 51 |
| P45$_{(555–566)}$ | GlyAspGluGlyGluThrAlaProLeuSerArgAla | SEQ ID NO: | 52 |
| P46$_{(563–574)}$ | LeuSerArgAlaGlyValValValPheAsnCysSer | SEQ ID NO: | 53 |
| P47$_{(603–614)}$ | LeuPheLeuValProSerProGlyValPheSerVal | SEQ ID NO: | 54 |
| P48$_{(605–616)}$ | LeuValProSerProGlyValPheSerValAlaGlu | SEQ ID NO: | 55 |
| P49$_{(707–718)}$ | GluLeuThrLeuCysSerArgLysLysGlySerLeu | SEQ ID NO: | 56 |
| P50$_{(712–723)}$ | SerArgLysLysGlySerLeuLysLeuProArgCys | SEQ ID NO: | 57 |
| P51$_{(717–728)}$ | SerLeuLysLeuProArgCysValThrProAspAsp | SEQ ID NO: | 58 |
| P52$_{(722–733)}$ | ArgCysValThrProAspAspAlaCysThrSerLeu | SEQ ID NO: | 59 |
| P53$_{(727–738)}$ | AspAspAlaCysThrSerLeuAspAlaThrMetIle | SEQ ID NO: | 60 |
| P54$_{(731–742)}$ | ThrSerLeuAspAlaThrMetIleTrpThrMetMet | SEQ ID NO: | 3 |
| P55$_{(732–743)}$ | SerLeuAspAlaThrMetIleTrpThrMetMetGln | SEQ ID NO: | 61 |
| P56$_{(737–748)}$ | MetIleTrpThrMetMetGlnAsnLysLysThrPhe | SEQ ID NO: | 62 |
| P57$_{(742–752)}$ | MetGlnAsnLysLysThrPheThrLysProLeuAla | SEQ ID NO: | 63 |
| P58$_{(747–758)}$ | ThrPheThrLysProLeuAlaValValLeuGlnVal | SEQ ID NO: | 64 |
| P59$_{(761–775)}$ | LysGluAsnValProSerThrLysAspSerSerProIleProPro | SEQ ID NO: | 65 |
| P60$_{(766–780)}$ | SerThrLysAspSerSerProIleProProProProProGlnIle | SEQ ID NO: | 66 |
| P61$_{(771–785)}$ | SerProIleProProProProProGlnIlePheHisGlyLeuAsp | SEQ ID NO: | 67 |
| P62$_{(776–780)}$ | ProProProGlnIlePheHisGlyLeuAspThrLeuThrValMet | SEQ ID NO: | 68 |
| P63$_{(781–795)}$ | PheHisGlyLeuAspThrLeuThrValMetGlyIleAlaPheAla | SEQ ID NO: | 69 |
| P64$_{(786–800)}$ | ThrLeuThrValMetGlyIleAlaPheAlaAlaPheValIleGly | SEQ ID NO: | 70 |
| P65$_{(797–809)}$ | LeuLeuThrGlyAlaLeuTrpTyrIleTyrSerHis | SEQ ID NO: | 71 |
| P66$_{(45–59)}$ | LeuMetGluSerPheThrValLeuSerGlyCysAlaSerArgGly | SEQ ID NO: | 72 |
| P67$_{(50–64)}$ | ThrValLeuSerGlyCysAlaSerArgGlyThrThrGlyLeuPro | SEQ ID NO: | 73 |
| P68$_{(55–69)}$ | CysAlaSerArgGlyThrThrGlyLeuProArgGluValHisVal | SEQ ID NO: | 74 |
| P69$_{(60–74)}$ | ThrThrGlyLeuProArgGluValHisValLeuAsnLeuArgSer | SEQ ID NO: | 75 |
| P70$_{(65–79)}$ | ArgGluValHisValLeuAsnLeuArgSerThrAspGlnGlyPro | SEQ ID NO: | 76 |
| P71$_{(70–84)}$ | LeuAsnL uArgSerThrAspGlnGlyProGlyGlnArgGlnArg | SEQ ID NO: | 77 |
| P72$_{(75–89)}$ | ThrAspGlnGlyProGlyGlnArgGlnArgGluValThrLeuHis | SEQ ID NO: | 78 |
| P73$_{(80–94)}$ | GlyGlnArgGlnArgGluValThrLeuHisLeuAsnProIleAla | SEQ ID NO: | 79 |
| P74$_{(85–99)}$ | GluValThrLeuHisLeuAsnProIleAlaSerValHisThrHis | SEQ ID NO: | 80 |
| P75$_{(90–104)}$ | LeuAsnProIleAlaSerValHisThrHisHisLysProIleVal | SEQ ID NO: | 81 |
| P76$_{(95–109)}$ | SerValHisThrHisHisLysProIleValPheLeuLeuAsnSer | SEQ ID NO: | 82 |
| P77$_{(100–114)}$ | HisLysProIleValPheLeuLeuAsnSerProGlnProLeuVal | SEQ ID NO: | 83 |
| P78$_{(105–119)}$ | PheLeuLeuAsnSerProGlnProLeuValTrpHisLeuLysThr | SEQ ID NO: | 84 |
| P79$_{(110–124)}$ | ProGlnProLeuValTrpHisLeuLysThrGluArgLeuAlaAla | SEQ ID NO: | 85 |
| P80$_{(115–129)}$ | TrpHisLeuLysThrGluArgLeuAlaAlaGlyValProArgLeu | SEQ ID NO: | 86 |
| P81$_{(120–134)}$ | ArgLeuAlaAlaGlyValProArgLeuPheLeuValSerGluGly | SEQ ID NO: | 87 |
| P82$_{(125–139)}$ | GlyValProArgLeuPheLeuValSerGluGlySerValValGln | SEQ ID NO: | 88 |
| P83$_{(130–144)}$ | PheLeuValSerGluGlySerValValGlnPheProSerGlyAsn | SEQ ID NO: | 89 |
| P84$_{(135–149)}$ | GlySerValValGlnPheProSerGlyAsnPheSerLeuThrAla | SEQ ID NO: | 90 |
| P85$_{(140–154)}$ | PheProSerGlyAsnPheSerLeuThrAlaGluThrGluGluArg | SEQ ID NO: | 91 |
| P86$_{(145–159)}$ | PheSerLeuThrAlaGluThrGluGluArgAsnPheProGlnGlu | SEQ ID NO: | 92 |
| P87$_{(150–164)}$ | GluThrGluGluArgAsnPheProGlnGluAsnGluHisLeuVal | SEQ ID NO: | 93 |

-continued

| Peptide | Sequence | | |
|---|---|---|---|
| P88(155–169) | AsnPheProGlnGluAsnGluHisLeuValArgTrpAlaGlnLys | SEQ ID NO: | 94 |
| P89(160–174) | AsnGluHisLeuValArgTrpAlaGlnLysGluTyrGlyAlaVal | SEQ ID NO: | 95 |
| P90(165–179) | ArgTrpAlaGlnLysGluTyrGlyAlaValThrSerPheThrGlu | SEQ ID NO: | 96 |
| P91(170–184) | GluTyrGlyAlaValThrSerPheThrGluLeuLysIleAlaArg | SEQ ID NO: | 97 |
| P92(175–189) | ThrSerPheThrGluLeuLysIleAlaArgAsnIleTyrIleLys | SEQ ID NO: | 98 |
| P93(180–194) | LeuLysIleAlaArgAsnIleTyrIleLysValGlyGluAspGln | SEQ ID NO: | 99 |
| P94(185–199) | AsnIleTyrIleLysValGlyGluAspGlnValPheProProThr | SEQ ID NO: | 100 |
| P95(190–201) | ValGlyGluAspGlnValPheProProThrCysAsnIleGlyLys | SEQ ID NO: | 101 |
| P96(195–209) | ValPheProProThrCysAsnIleGlyLysAsnPheLeuSerLeu | SEQ ID NO: | 102 |
| P97(200–214) | CysAsnIleGlyLysAsnPheLeuSerLeuAsnTyrLeuAlaGlu | SEQ ID NO: | 103 |
| P98(205–219) | AsnPheLeuSerLeuAsnTyrLeuAlaGluTyrLeuGlnProLys | SEQ ID NO: | 104 |
| P99(210–224) | AsnTyrLeuAlaGluTyrLeuGlnProLysAlaAlaGluGlyCys | SEQ ID NO: | 105 |
| P100(215–229) | TyrLeuGlnProLysAlaAlaGluGlyCysValLeuProSerGln | SEQ ID NO: | 106 |
| P101(220–234) | AlaAlaGluGlyCysValLeuProSerGlnProHisGluLysGlu | SEQ ID NO: | 107 |
| P102(225–239) | ValLeuProSerGlnProHisGluLysGluValHisIleIleGlu | SEQ ID NO: | 108 |
| P103(230–244) | ProHisGluLysGluValHisIleIleGluLeuIleThrProSer | SEQ ID NO: | 109 |
| P104(235–249) | ValHisIleIleGluLeuIleThrProSerSerAsnProTyrSer | SEQ ID NO: | 110 |
| P105(240–254) | LeuIleThrProSerSerAsnProTyrSerAlaPheGlnValAsp | SEQ ID NO: | 111 |
| P110(265–279) | AspProGluValValLysAsnLeuValLeuIleLeuLysCysLys | SEQ ID NO: | 115 |
| P111(270–284) | LysAsnLeuValLeuIleLeuLysCysLysLysSerValAsnTrp | SEQ ID NO: | 116 |
| P112(275–289) | IleLeuLysCysLysLysSerValAsnTrpValIleLysSerPhe | SEQ ID NO: | 117 |
| P113(280–294) | LysSerValAsnTrpValIleLysSerPheAspValLysGlyAsn | SEQ ID NO: | 118 |
| P114(285–299) | ValIleLysSerPheAspValLysGlyAsnLeuLysValIleAla | SEQ ID NO: | 119 |
| P115(290–304) | AspValLysGlyAsnLeuLysValIleAlaProAsnSerIleGly | SEQ ID NO: | 120 |
| P106(245–259) | SerAsnProTyrSerAlaPheGlnValAspIleIleValAspIle | SEQ ID NO: | 4 |
| P107(250–264) | AlaPheGlnValAspIleIleValAspIleArgProAlaGlnGlu | SEQ ID NO: | 112 |
| P108(255–269) | IleIleValAspIleArgProAlaGlnGluAspProGluValVal | SEQ ID NO: | 113 |
| P109(260–274) | ArgProAlaGlnGluAspProGluValValLysAsnLeuValLeu | SEQ ID NO: | 114 |
| P116(295–309) | LeuLysValIleAlaProAsnSerIleGlyPheGlyLysGluSer | SEQ ID NO: | 121 |
| P117(300–314) | ProAsnSerIleGlyPheGlyLysGluSerGluArgSerMetThr | SEQ ID NO: | 122 |
| P118(305–319) | PheGlyLysGluSerGluArgSerMetThrMetThrLysLeuVal | SEQ ID NO: | 123 |
| P119(310–324) | GluArgSerMetThrMetThrLysLeuValArgAspAspIlePro | SEQ ID NO: | 124 |
| P120(315–329) | MetThrLysLeuValArgAspAspIleProSerThrGlnGluAsn | SEQ ID NO: | 125 |
| P121(320–334) | ArgAspAspIleProSerThrGlnGluAsnLeuMetLysTrpAla | SEQ ID NO: | 126 |
| P122(325–339) | SerThrGlnGluAsnLeuMetLysTrpAlaLeuAspAsnGlyTyr | SEQ ID NO: | 127 |
| P123(330–344) | LeuMetLysTrpAlaLeuAspAsnGlyTyrArgProValThrSer | SEQ ID NO: | 128 |
| P124(335–349) | LeuAspAsnGlyTyrArgProValThrSerTyrThrMetAlaPro | SEQ ID NO: | 129 |
| P125(340–354) | ArgProValThrSerTyrThrMetAlaProValAlaAsnArgPhe | SEQ ID NO: | 130 |
| P126(345–339) | TyrThrMetAlaProValAlaAsnArgPheHisLeuArgLeuGlu | SEQ ID NO: | 131 |
| P127(350–364) | ValAlaAsnArgPheHisLeuArgLeuGluAsnAsnGluGluMet | SEQ ID NO: | 132 |
| P128(355–369) | HisLeuArgLeuGluAsnAsnGluGluMetArgAspGluGluVal | SEQ ID NO: | 133 |
| P129(360–374) | AsnAsnGluGluMetArgAspGluGluValHisThrIleProPro | SEQ ID NO: | 134 |
| P130(365–379) | ArgAspGluGluValHisThrIleProProGluLeuArgIleLeu | SEQ ID NO: | 135 |
| P131(370–384) | HisThrIleProProGluLeuArgIleLeuLeuAspProAspHis | SEQ ID NO: | 136 |
| P132(375–389) | GluLeuArgIleLeuLeuAspProAspHisProProAlaLeuAsp | SEQ ID NO: | 137 |
| P133(300–394) | LeuAspProAspHisProProAlaLeuAspAsnProLeuPhePro | SEQ ID NO: | 138 |
| P134(385–399) | ProProAlaLeuAspAsnProLeuPheProGlyGluGlySerPro | SEQ ID NO: | 139 |
| P135(390–404) | AsnProLeuPheProGlyGluGlySerProAsnGlyGlyLeuPro | SEQ ID NO: | 140 |
| P136(395–409) | GlyGluGlySerProAsnGlyGlyLeuProPhePheProPheAsp | SEQ ID NO: | 141 |
| P137(400–414) | AsnGlyGlyLeuProPheProPheProAspIleProArgArgGly | SEQ ID NO: | 142 |
| P138(405–419) | PheProPheProAspIleProArgArgGlyTrpLysGluGlyGlu | SEQ ID NO: | 143 |

The peptides in Table 4 were tested for their capacity to block TGFβ1 in the model of inhibition of the MV-1-Lu cell line. Since TGFβ1 is able to inhibit the growth of this line, inhibition of TGFβ1 by the peptides would be able to re-establish cell growth. These tests are shown in FIGS. 9 to 12.

As can be seen in FIGS. 9 to 12, there are various peptides that are able to inhibit the growth of the MV-1-Lu cell line to a greater or lesser degree, but only peptide P54 is capable of inhibiting the activity of TGFβ1 almost completely. With the aim of conducting a more thorough investigation of this peptide, tests were carried out using different concentrations of peptide against a fixed concentration of TGFβ1 of 200 pg/ml.

Dose-Response Test of the Inhibition of TGFβ1 by Peptide P54

The effect of the concentration of peptide P54 on inhibition of the activity of TGFβ1 was investigated. In view of the low solubility of this peptide, stock solutions with nominal concentration of peptide were prepared, as was done in the case of peptide P12, and aliquots were taken from them, and filtered, or even used directly for the inhibition tests.

Figure 13:
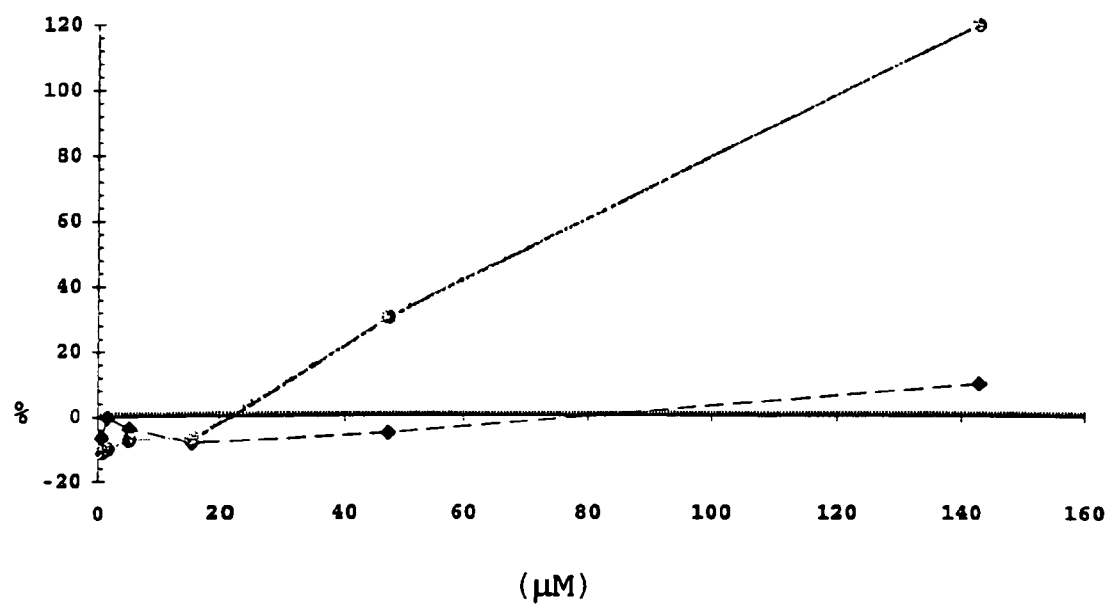
FIG. 13. Percentage inhibition of the activity of TGFβ1 (200 pg/ml) in the presence of different nominal concentrations of peptide P54, filtered (♦) and unfiltered (●).

FIG. 13 examines the inhibitory effect of nominal concentrations of peptide, before and after filtration. It can be seen that there is no measurable inhibitory activity in the filtrate of peptide P54.

Having verified the capacity of peptide P54 to inhibit the activity of TGFβ1 in a manner that depends on the dose used, we proceeded to synthesize new peptides, taking as a basis the sequence of P54, with the aim of trying to improve the solubility and hence its activity at lower doses. Two peptides derived from the human type III receptor were also synthesized. One of these peptides (P144) is equivalent to peptide P54. The other peptide (P145) is similar to peptide P106 of the type III receptor of the rat, which had also demonstrated activity. These new peptides are shown in Table 5.

TABLE 5

Peptides derived from modification of peptide P54 (peptides P139 to P143) and of the human type III receptor (peptides P144 and P145).

| Peptide | Sequence | Derivation | | |
|---|---|---|---|---|
| P54(731–743) | ThrSerLeuAspAlaThrMetIleTrpThrMetMet | Rat type III receptor | SEQ ID NO: | 3 |
| P139 | ThrSerLeuAspAlaThrMetIleTrpAspAspAsp | | SEQ ID NO: | 144 |
| P140 | AspAspAspAlaThrMetIleTrpThrMetMet | | SEQ ID NO: | 145 |
| P141 | AspAlaThrMetIleTrpAsp | | SEQ ID NO: | 146 |
| P142 | ThrSerLeuMetIleTrpThrMetMet | | SEQ ID NO: | 5 |
| P143 | ThrSerLeuAspAlaThrThrMetMet | | SEQ ID NO: | 147 |
| P144(728–743) | ThrSerLeuAspAlaSerIleIleTrpAlaMetMetGlnAsn | Human type III receptor | SEQ ID NO: | 6 |
| P145(241–254) | SerAsnProTyrSerAlaPheGlnValAspIleThrIleAsp | Human type III receptor | SEQ ID NO: | 7 |

Figure 14:
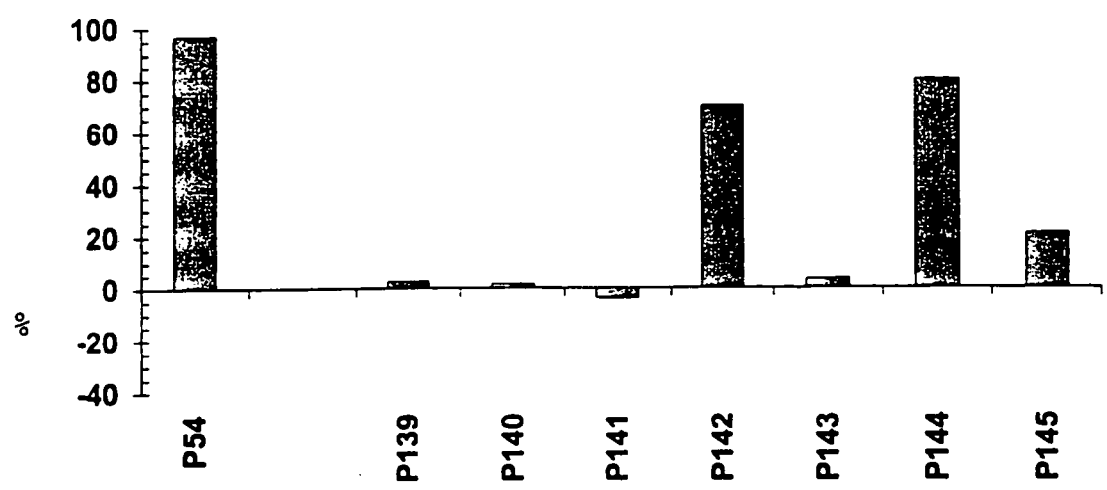
FIG. 14. Percentage inhibition of TGFβ1 (200 pg/ml) by receptor peptides derived from modification of peptide P54 (P139 to P143) and of the peptides derived from the human type III receptor (P144 and P145). All the peptides were tested at a concentration of 200 μg/ml. Inhibition of TGFβ1 of 100% corresponds to the growth of MV-1-Lu cells that is obtained in the absence of TGFβ1.

The test of activity of the peptides in Table 5 is shown in FIG. 14.

Dose-Response Test of Inhibition of TGFβ1 by Peptide P144

Figure 15:
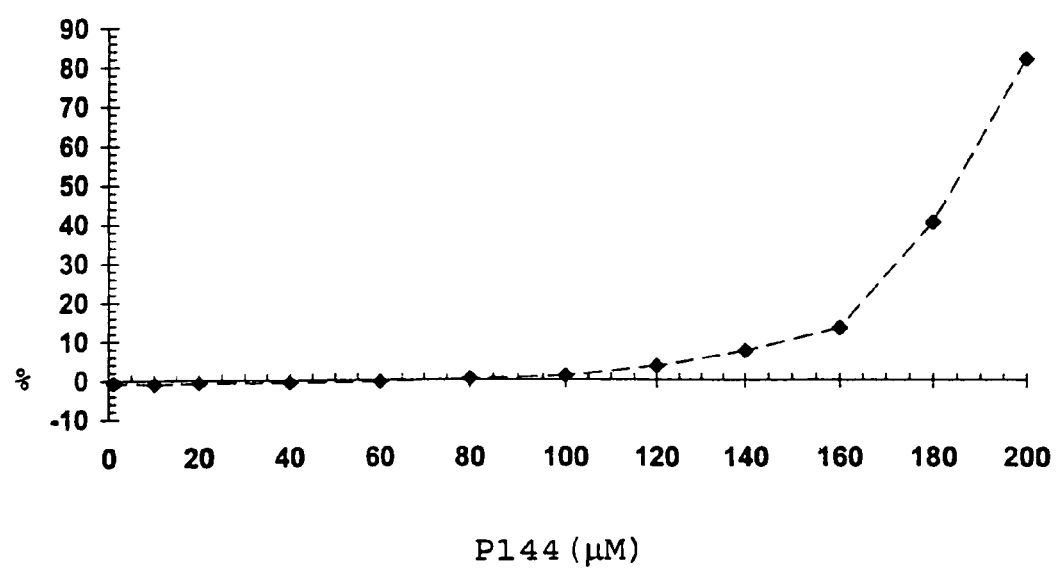
FIG. 15. Percentage inhibition of the activity of TGFβ1 (200 pg/ml) in the presence of different nominal concentrations of peptide P144 without filtration.

A dose-response test was carried out with peptide P144 derived from the sequence of the human type III receptor, with the aim of testing whether its activity was dependent on the concentration (FIG. 15). It can be seen that the activity of the peptide decreases with the decrease in the concentration of peptide used in the tests.

Tests of Inhibition of the Binding of TGFβ1 to its Receptors by Peptide P144 (Affinity Labelling)

Peptide P144 derived from the sequence of the human type III receptor was used in affinity labelling tests for verifying its ability to inhibit the binding of TGFβ1 to its cell receptors (Material and Methods).

Owing to the different activity of the batches of $^{125}$I-TGFβ1 employed, the concentrations of peptide used in the tests were adjusted according to the concentration of the $^{125}$I-TGFβ1 batch used in each case. The results of these tests are shown in FIG. 15.

After verifying inhibition of the binding of TGFβ1 to its cell receptors by peptide P144, a new test was conducted with the aim of titrating peptide P144. It was observed that the peptide lost its activity at a concentration of $2 \times 10^5$ times the molar concentration of $^{125}$I-TGFβ1.

Inhibition of TGFβ1 by Peptides Derived from Other Proteins with Ability to Bind to TGFβ1 and Predicted as Complementary to TGFβ1

The peptides in Table 6, derived from proteins capable of binding to TGFβ1, were synthesized in this series.

Table 6. Peptides derived from various proteins capable of binding to TGFβ1 (type II receptor P146, fetuin P147 to P149, endoglin P150 to P154 and α2-macroglobulin P155 to P179). The number of the peptide is shown, together with its position in the complete sequence, its amino acid sequence, and its origin. For convenience of synthesis, all the peptides were synthesized with an alanine added at the C-terminal end which is not shown in the table.

| Peptide | Sequence | Origin | | |
|---|---|---|---|---|
| P146(84–101) | CysValAlaValTrpArgLysAsnAsp-GluAsnIleThrLeuGluThrValCys | Type II receptor | SEQ ID NO: | 148 |
| P147(114–133) | CysAspPheGlnLeuLeuLysLeuAspG-lyLysPheSerValValTyrAlaLysCys | Fetuin | SEQ ID NO: | 149 |
| P148(114–133) | CysAspPheHisIleLeuLysGlnAspG-lyGlnPheArgValCysHisAlaGlnCys | Fetuin | SEQ ID NO: | 150 |
| P149(114–133) | CysAspIleHisValLeuLysGlnAspG-lyPheSerValLeuPheThrLysCysAsp | Fetuin | SEQ ID NO: | 151 |
| P150(247–261) | GluAlaValLeuIleLeuGlnGlyPro-ProTyrValSerTrpLeu | Endoglin | SEQ ID NO: | 8 |
| P151(289–303) | ValAsnLeuProAspThrArgGlnG-lyLeuLeuGluGluAlaArg | Endoglin | SEQ ID NO: | 152 |
| P152(445–459) | LeuAspSerLeuSerPheGlnLeuG-lyLeuTyrLeuSerProHis | Endoglin | SEQ ID NO: | 9 |
| P153(481–495) | ProSerIleProGluLeuMetThrGln-LeuAspSerCysGlnLeu | Endoglin | SEQ ID NO: | 153 |

-continued

| Peptide | Sequence | Origin | |
|---|---|---|---|
| P154(479–493) | MetSerProSerIleProGluLeu-MetThrGlnLeuAspSerCys | Endoglin | SEQ ID NO: 154 |
| P155(13–34) | LeuLeuLeuLeuValLeuLeuProThrAspAlaSer | α-2-Macroglobulin | SEQ ID NO: 155 |
| P156(30–51) | ProThrAspAlaSerValSerGlyLysProGlnTyr | α-2-Macroglobulin | SEQ ID NO: 156 |
| P157(44–65) | ThrGluLysGlyCysValLeuLeuSerTyrLeuAsn | α-2-Macroglobulin | SEQ ID NO: 157 |
| P158(166–177) | TyrIleGlnAspProLysGlyAsnArgIleAlaGln | α-2-Macroglobulin | SEQ ID NO: 158 |
| P158(166–177) | TyrIleGlnAspProLysGlyAsnArgIleAlaGln | α-2-Macroglobulin | SEQ ID NO: 158 |
| P159(193–202) | PheProLeuSerSerGluProPheGlnGlySerTyr | α-2-Macroglobulin | SEQ ID NO: 159 |
| P160(247–258) | AsnValSerValCysGlyLeuTyrThrTyrGlyLys | α-2-Macroglobulin | SEQ ID NO: 160 |
| P161(246–259) | ValSerValCysGlyLeuTyrThrTyrGlyLysPro | α-2-Macroglobulin | SEQ ID NO: 161 |
| P162(250–262) | ValCysGlyLeuTyrThrTyrGlyLysProValPro | α-2-Macroglobulin | SEQ ID NO: 162 |
| P163(267–278) | SerIleCysArgLysTyrSerAspAlaSerAspCys | α-2-Macroglobulin | SEQ ID NO: 163 |
| P164(469–480) | ProCysGlyHisThrGlnThrValGlnAlaHisTyr | α-2-Macroglobulin | SEQ ID No: 164 |
| P165(354–365) | AspSerAlaLysTyrAspValGluAsnCysLeuAla | α-2-Macroglobulin | SEQ ID NO: 165 |
| P167(790–801) | GlnProPhePheValGluLeuThrMetProTyrSer | α-2-Macroglobulin | SEQ ID NQ: 167 |
| P168(827–628) | GlnLeuGluAlaSerProAlaPheLeuAlaValPro | α-2-Macroglobulin | SEQ ID NO: 168 |
| P169(835–836) | SerValGlnLeuGluAlaSerProAlaPheLeuAla | α-2-Macroglobulin | SEQ ID NO: 169 |
| P170(876–887) | AlaLeuGluSerGlnGluLeuCysGlyThrGluVal | α-2-Macroglobulin | SEQ ID NO: 170 |
| P171(1001–1012) | LysSerLysIleGlyTyrLeuAsnThrGlyTyr | α-2-Macroglobulin | SEQ ID NO: 171 |
| P172(1013–1026) | IleGlyTyrLeuAsnThrGlyTyrGlnArgGlnLeu | α-2-Macroglobulin | SEQ ID NO: 172 |
| P173(1062–1073) | LysArgLysGluValLeuLysSerLeuAsnGluGlu | α-2-Macroglobulin | SEQ ID NO: 173 |
| P174(1193–1204) | ValGlyHisPheTyrGluProGlnAlaProSerAla | α-2-Macroglobulin | SEQ ID NO: 174 |
| P175(1209–1220) | ThrSerTyrValLeuLeuAlaTyrLeuThrGlnAla | α-2-Macroglobulin | SEQ ID NO: 175 |
| P176(1211–1222) | TyrValLeuLeuAlaTyrLeuThrAlaGlnProAla | α-2-Macroglobulin | SEQ ID NO: 176 |
| P177(1234–1367) | ValAlaLeuHisAlaLeuSerLysTyrGlyAlaAla | α-2-Macroglobulin | SEQ ID NO: 177 |
| P178(1233–1343) | TyrGlyArgAsnGlnGlyAsnThrTrpLeuThrAla | α-2-Macroglobulin | SEQ ID NO: 178 |
| P179(1234–1345) | ArgAsnGlnGlyAsnThrTrpLeuThrAlaPheVal | α-2-Macroglobulin | SEQ ID NO: 179 |

Figure 17:
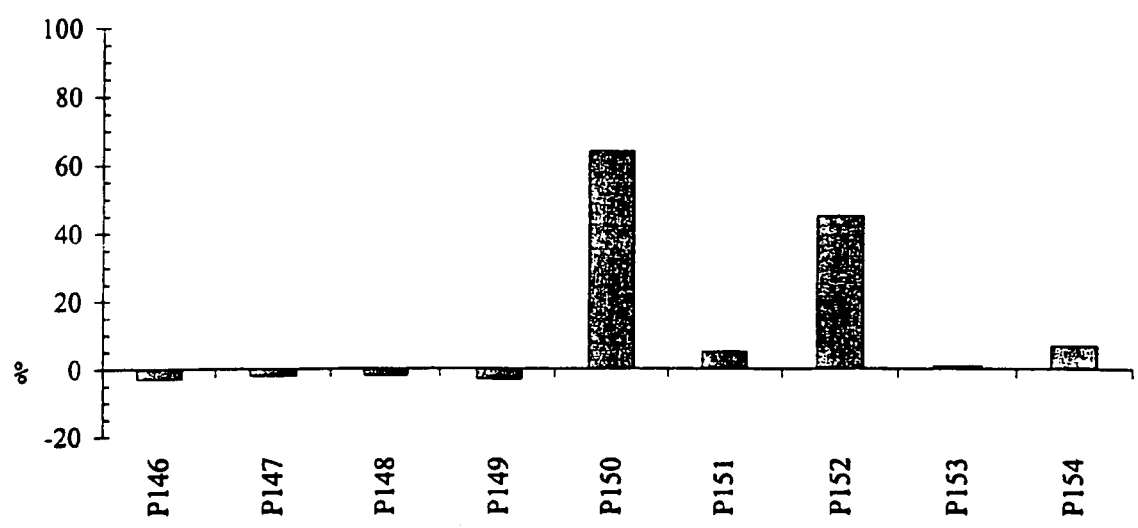
FIG. 17. Percentage inhibition of TGFβ1 (200 pg/ml) by peptides derived from human type II receptor (P146), from fetuin (P147 to P149) and from endoglin (P150 to P154). All the peptides were tested at a concentration of 200 μg/ml. Inhibition of TGFβ1 of 100% corresponds to the growth of MV-1-Lu cells that is obtained in the absence of TGFβ1.
Figure 18:
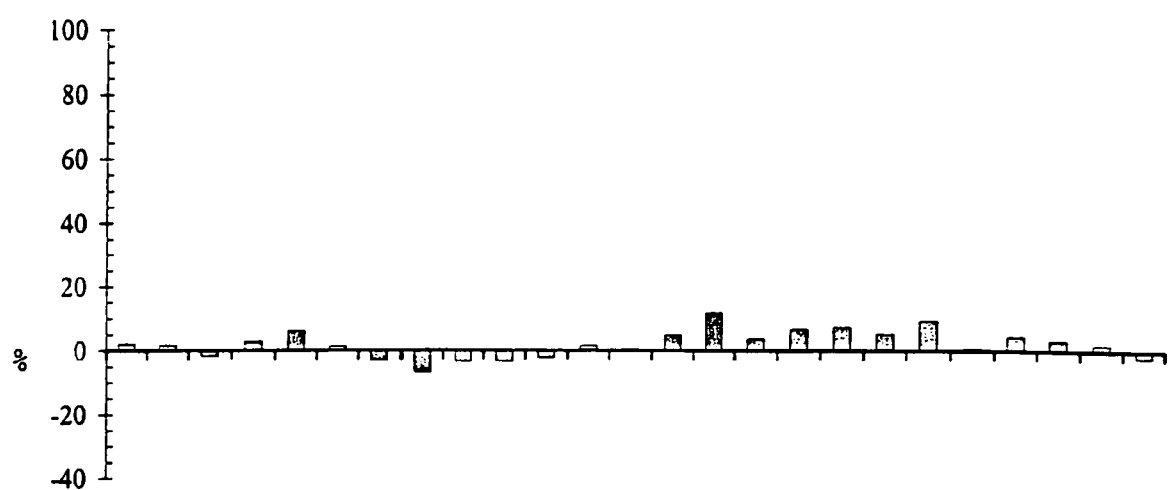
FIG. 18. Percentage inhibition of TGFβ1 (200 pg/ml) by peptides derived from α2-macroglobulin. All the peptides were tested at a concentration of 200 μg/ml. Inhibition of TGFβ1 of 100% corresponds to the growth of MV-1-Lu cells that is obtained in the absence of TGFβ1.

FIGS. 17 and 18 show the inhibitory activity of the peptides derived from Table 10.

As can be seen in FIGS. 17 and 18, only peptide P150 showed activity greater than 50%. However, peptides P146 and P149, which had been described as active by Demetriou M et al. (1996) J. Biol. Chem. 271:12755–12761, were not found to be active under the conditions employed for this test.

Figure 19:
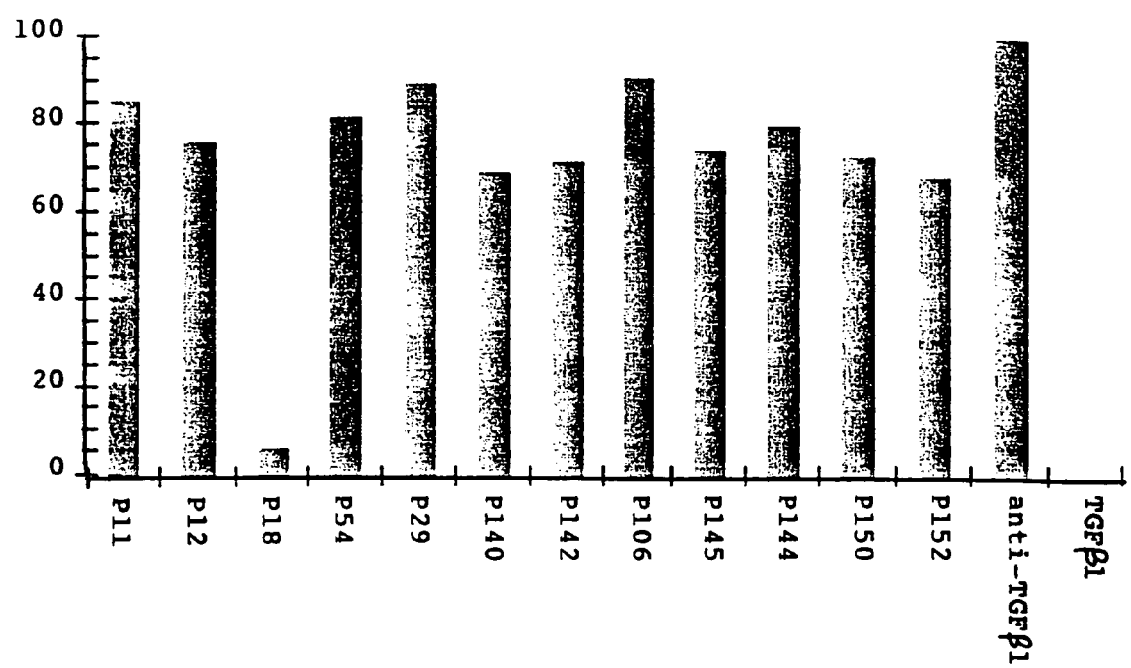
FIG. 19. Percentage inhibition of the binding of TGFβ1 to MV-1-Lu cells by various synthetic peptides. Inhibition was investigated by measuring the percentage of labelled cells (emit fluorescence) and unlabelled cells (do not emit fluorescence) for each peptide (Material and Methods).

Measurement by Flow Cytometry of the Inhibitory Effect of Synthetic Peptides on the Binding of TGFβ1 to its Cell Receptors Peptides derived from previous syntheses, both those that were synthesized from the sequence of TGFβ1 and those from the type III receptor, were used for measuring, by flow cytometry, their capacity to inhibit the binding of TGFβ1 to the cell receptors. In these tests the cells are incubated with the peptide before adding TGFβ1-biotin, which will be detected using avidin-FITC (Material and Methods). Then the fluorescence emitted by the avidin-FITC is measured: this will be directly proportional to the quantity of TGFβ1 bound to the cells and inversely proportional to the activity of the peptide. The results obtained with the most relevant peptides are shown in FIG. 19 and Table 7.

TABLE 7

Comparison of the inhibitory activity of TGFβ1, of some peptides, measured by bioassay of inhibition of growth of the MV-1-Lu[1] cells (peptide concentration 200 μg/ml) with inhibition of the binding of TGFβ1 to its cell receptors measured using flow cytometry[2] (peptide concentration 420 μg/ml).

| Peptides | Bioassay (% inhibition)[1] | Cytometry % inhibition[2] | Sequence | |
|---|---|---|---|---|
| P29 | 77.6 | 92.34 | HisGluProLysGlyTyrHisAlaAsnPheCysLeuGlyProCysProTyrIleTrpSerLeuAspThr | SEQ ID NO: 10 |
| P11 | 40 | 86 | HisAlaAsnPheCysLeuGlyProCysProTyrIleTrpSerLeu | SEQ ID NO: 1 |
| P12 | 96 | 77 | PheCysLeuGlyProCysProTyrIleTrpSerLeuAspThr | SEQ ID NO: 2 |
| P18 | 18.2 | 6.5 | LeuTyrAsnGlnHisAsnProGlyAlaSerAlaAlaProCysCys | SEQ ID NO: 26 |
| P54 | 97 | 82.3 | ThrSerLeuAspAlaThrMetIleTrpThrMetMet | SEQ ID NO: 3 |

TABLE 7-continued

Comparison of the inhibitory activity of TGFβ1, of some peptides, measured by bioassay of inhibition of growth of the MV-1-Lu[1] cells (peptide concentration 200 µg/ml) with inhibition of the binding of TGFβ1 to its cell receptors measured using flow cytometry[2] (peptide concentration 420 µg/ml).

| Peptides | Bioassay (% inhibition)[1] | Cytometry % inhibition)[2] | Sequence | | |
|---|---|---|---|---|---|
| P140 | −1.7 | 69.8 | AspAspAspAlaThrMetIle TrpThrMetMet | SEQ ID NO: | 145 |
| P142 | 70 | 72 | ThrSerLeuMetIleTrpThr MetMet | SEQ ID NO: | 5 |
| P106 | 40 | 91 | SerAsnProTyrSerAlaPhe GlnValAspIleIleValAsp Ile | SEQ ID NO: | 4 |
| P145 | 21 | 74.35 | SerAsnProTyrSerAlaPhe GlnValAspIleThrIleAsp | SEQ ID NO: | 7 |
| P144 | 88 | 80 | ThrSerLeuAspAlaSerIle IleTrpAlaMetMetGlnAsn | SEQ ID NO: | 6 |
| P150 | 64 | 73 | GluAlaValLeuIleLeuGln GlyProProTyrValSerTrp Leu | SEQ ID NO: | 8 |
| P152 | 45 | 68.4 | LeuAspSerLeuSerPheGln LeuGlyLeuTyrLeuSerPro His | SEQ ID NO: | 9 |

Inhibition In Vivo of the Activity of TGFβ1

Peptide P144 derived from the sequence of the human type III receptor, which had proved active in the bioassays of inhibition of growth of the MV-1-Lu cell line, was used in the tests in vivo for studying its inhibitory effect in the induction of experimental cirrhosis with $CCl_4$, in a rat model.

Model of Experimental Cirrhosis in Wistar Rats

In this model, hepatic cirrhosis is induced by inhalation of carbon tetrachloride, for 11 weeks, twice per week (López Novoa J M et al. (1976) Patologia IX:223–240; Camps J. et al. (1987) Gastroenterology 93:498–505) as described in Material and Methods.

Figure 20:
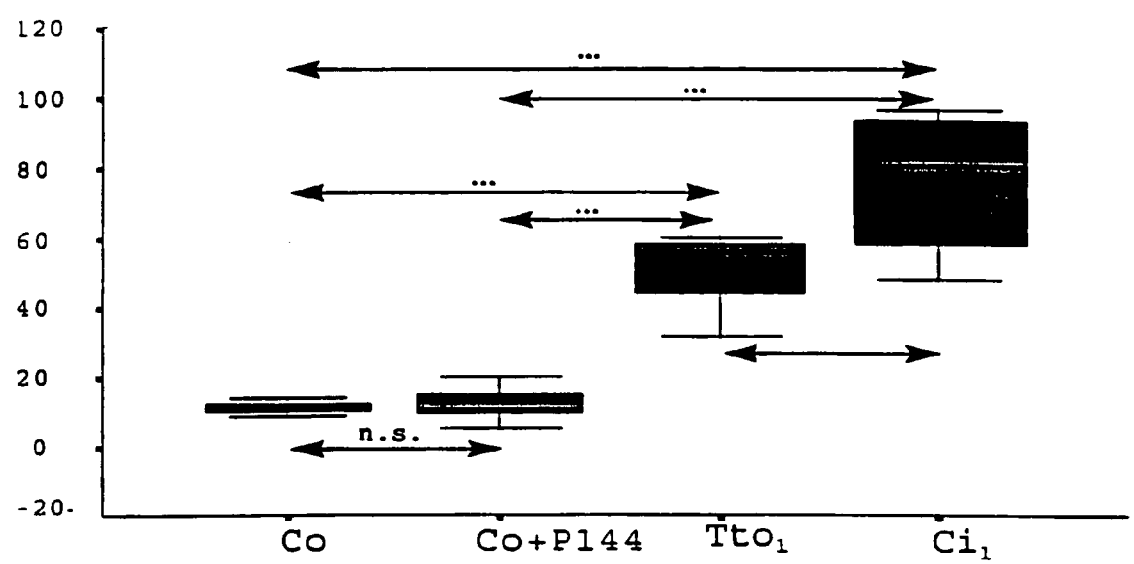
FIG. 20. Effect of administration of peptide P144 on collagen synthesis during experimental cirrhosis induction with $CCl_4$. The ratio of collagen to total protein is shown on the ordinate. The abscissa shows the various groups of rats: Co=healthy rats; Co+P144=healthy rats treated with peptide P144; $Tto_1$=rats subjected to induction of cirrhosis with $CCl_4$ and administered peptide P144 on alternate days during this period and $Ci_1$=rats subjected to induction of cirrhosis with $CCl_4$ for 11 weeks and not treated with peptide P144.
Figure 21:
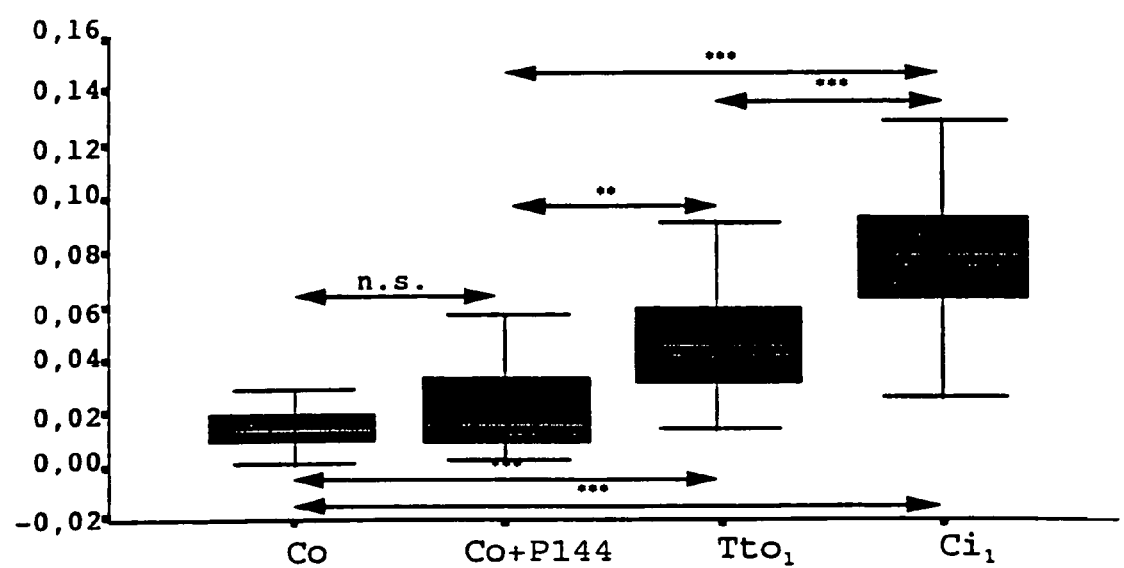
FIG. 21. Effect administration of peptide P144 on collagen synthesis during experimental cirrhosis induction with $CCl_4$. The ordinate shows the ratio of the area of fibrosis to the total area in tissue preparations stained with Sirius Red. The abscissa shows the various groups of rats: Co=healthy rats; Co+P144=healthy rats treated with the peptide; $Tto_1$=rats subjected to induction of cirrhosis with $CCl_4$ and administered peptide P144 on alternate days during this period and $Ci_1$=rats subjected to induction of cirrhosis with $CCl_4$ for 11 weeks and not treated with peptide P144.
Figure 22:
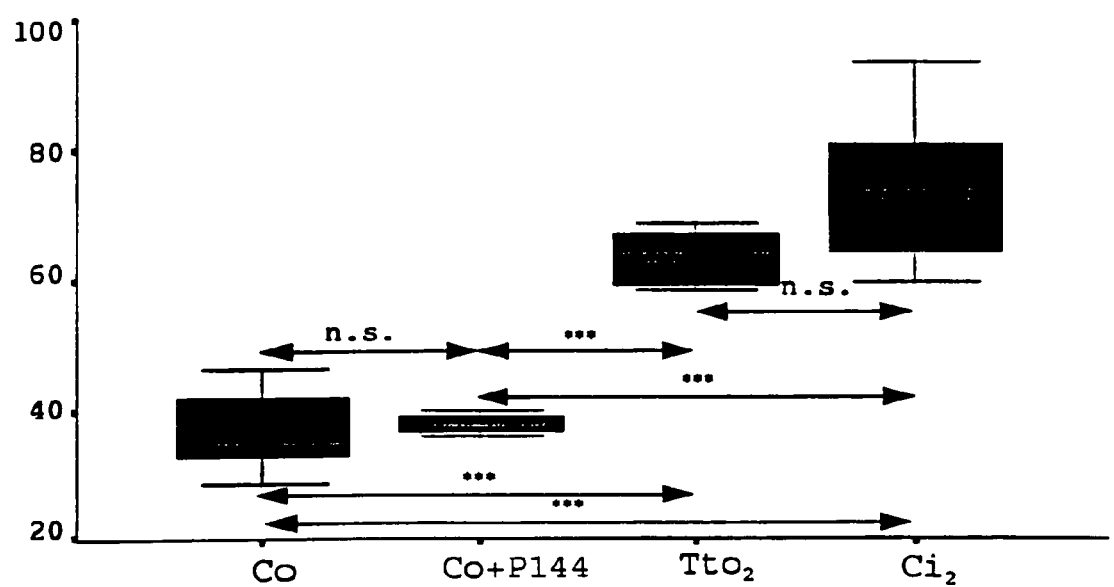
FIG. 22. Effect of administration of peptide P144 on collagen synthesis once cirrhosis has been induced with $CCl_4$. The ordinate shows the ratio of collagen to total protein. The abscissa shows the various groups of rats: Co=healthy rats; Co+P144=healthy rats treated with the peptide; $Tto_2$=rats subjected to induction of cirrhosis with $CCl_4$ and administered peptide P144 on alternate days at the end of this period and $Ci_2$=rats subjected to induction of cirrhosis with $CCl_4$ for 11 weeks and not treated with peptide P144.
Figure 23:
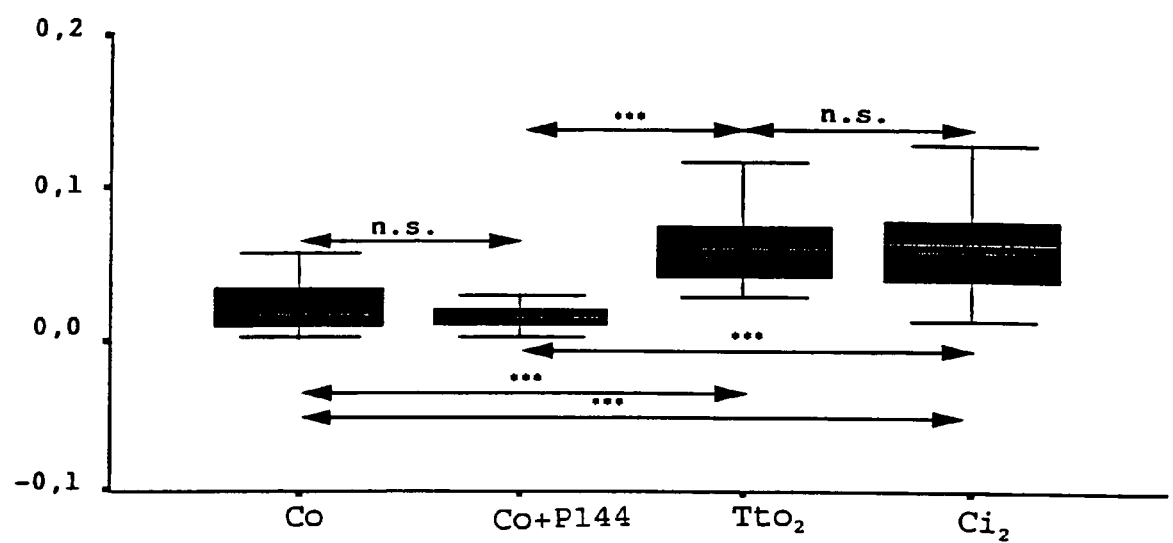
FIG. 23. Effect of administration of peptide P144 on collagen synthesis once cirrhosis has been induced with $CCl_4$. The ordinate shows the ratio of the area of fibrosis to the total area in tissue preparations. The abscissa shows the various groups of rats: Co=healthy rats; Co+P144=healthy rats treated with the peptide; $Tto_2$=rats subjected to induction of cirrhosis with $CCl_4$ and administered peptide P144 on alternate days at the end of this period and $Ci_2$=rats subjected to induction of cirrhosis with $CCl_4$ for 11 weeks and not treated with peptide P144.

Peptide P144 was administered in accordance with two protocols:

1. Protocol 1: The peptide was administered on alternate days by the intraperitoneal route during the cirrhosis induction process (11 weeks). FIGS. 20 and 21.
2. Protocol 2: The peptide was administered on alternate days by the intraperitoneal route for 3 weeks, once cirrhosis was established, i.e. at 12 weeks from the start of induction of cirrhosis. FIGS. 22 and 23.

The production of collagen in both protocols was measured by two techniques:

FIGS. 36 and 38 show total collagen production measured by staining liver sections (two per animal) with Fast Green and Direct Red, elution of the colour and reading in a spectrophotometer (Material and Methods) (López de León A. and Rojkind (1985) Histochem. Cytochem. 33:737–743; Gaudio E. et al. (1993) Int. J. Exp. Path. 74:463–469).

FIGS. 21 and 23 show collagen production, measured by image analysis of liver sections stained with Sirius Red, using light microscopy (Material and Methods).

As can be seen in FIG. 20, significant differences are observed ($P<0.05$) between the group of rats treated with peptide P144 ($Tto_1$) and the control group of cirrhotic rats ($Ci_1$) on investigating the ratio of collagen to total protein. In FIG. 37, the differences between the group of rats treated with peptide P144 ($Tto_1$) and the control group of cirrhotic rats ($Ci_1$) are also significant ($P<0.001$) when the area of fibrosis is investigated.

As can be seen in FIGS. 22 and 23, which show the results for the rats treated once cirrhosis was established, the differences between the groups of rats treated with peptide P144 ($Tto_2$) and the cirrhotic rats without treatment ($Ci_2$) are not significant when using either of the two techniques for measuring fibrosis.

Figure 24:
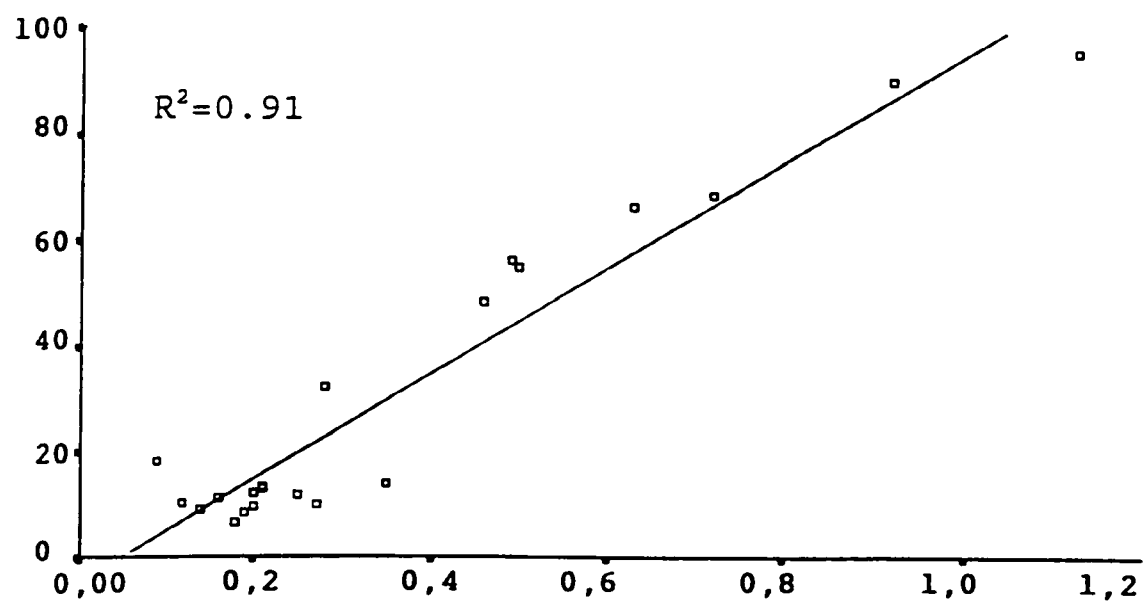
FIG. 24. Comparison of the data on quantity of collagen and area of fibrosis, obtained by the two techniques employed. The abscissa shows the values of the ratio of the area of fibrosis to the total area, obtained by image analysis. The ordinate shows the values of the ratio of pg of collagen to mg of total protein, obtained by spectrophotometric analysis of liver sections stained with Direct Red and Fast Green. $R^2$ is shown. ($F \leq 0.001$).
Figure 25:
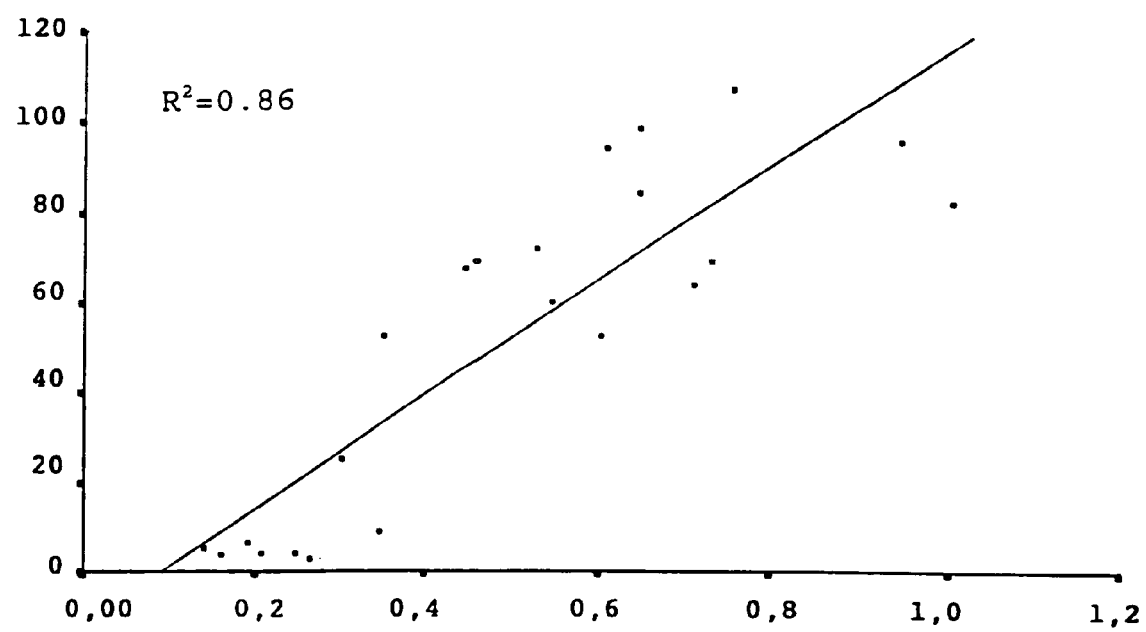
FIG. 25. Comparison of the data on quantity of collagen and area of fibrosis, obtained by the two techniques employed for examining the samples at the end of protocol 2. The abscissa shows the values of the ratio of the area of fibrosis to the total area, obtained by image analysis. The ordinate shows the values of the ratio of μg of collagen to mg of total protein, obtained by spectrophotometric analysis of liver sections stained with Direct Red and Fast Green. $R^2$ is shown. ($F \leq 0.001$)

The two techniques employed for measuring collagen were compared using linear regression with the aim of verifying the randomness of selection of the fields for investigation in each preparation and hence the validity of the image analysis, FIGS. 24 and 25.

As can be seen from FIGS. 24 and 25, there is a correlation between the two techniques with $R>0.85$ in both cases, which is highly significant ($F \leq 0.001$). This confirms that acquisition of the images for investigation was effected entirely randomly and hence confirms the validity of the data obtained by image analysis.

Figure 26:
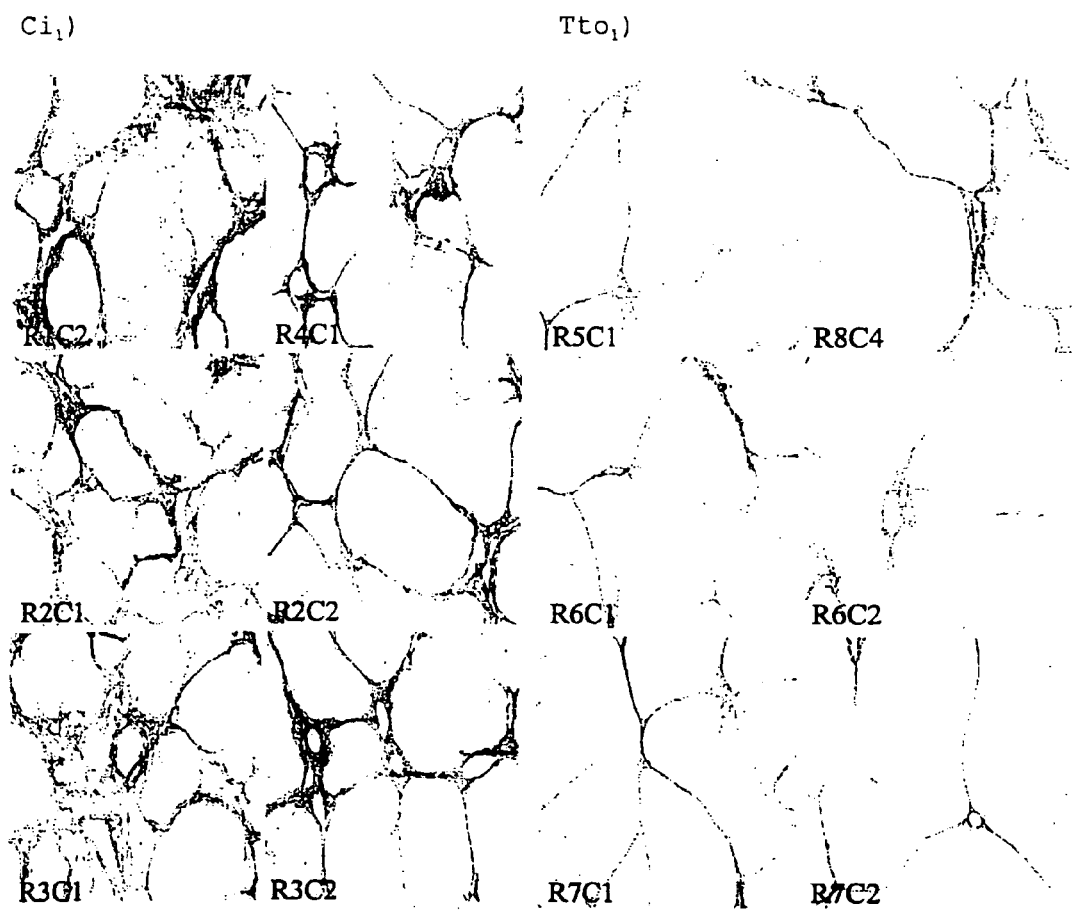
FIG. 26. Images that are representative of the 24 fields obtained by light microscopy (10×) from rat liver preparations stained with Sirius Red. Cirrhotic rats ($Ci_1$) at the end of induction of cirrhosis with $CCl_4$ and cirrhotic rats treated ($Tto_1$) with peptide P144 during induction of cirrhosis with CCl$_4$. Different fields were taken from preparations obtained from each animal (R=rat and C=field)
Figure 27:
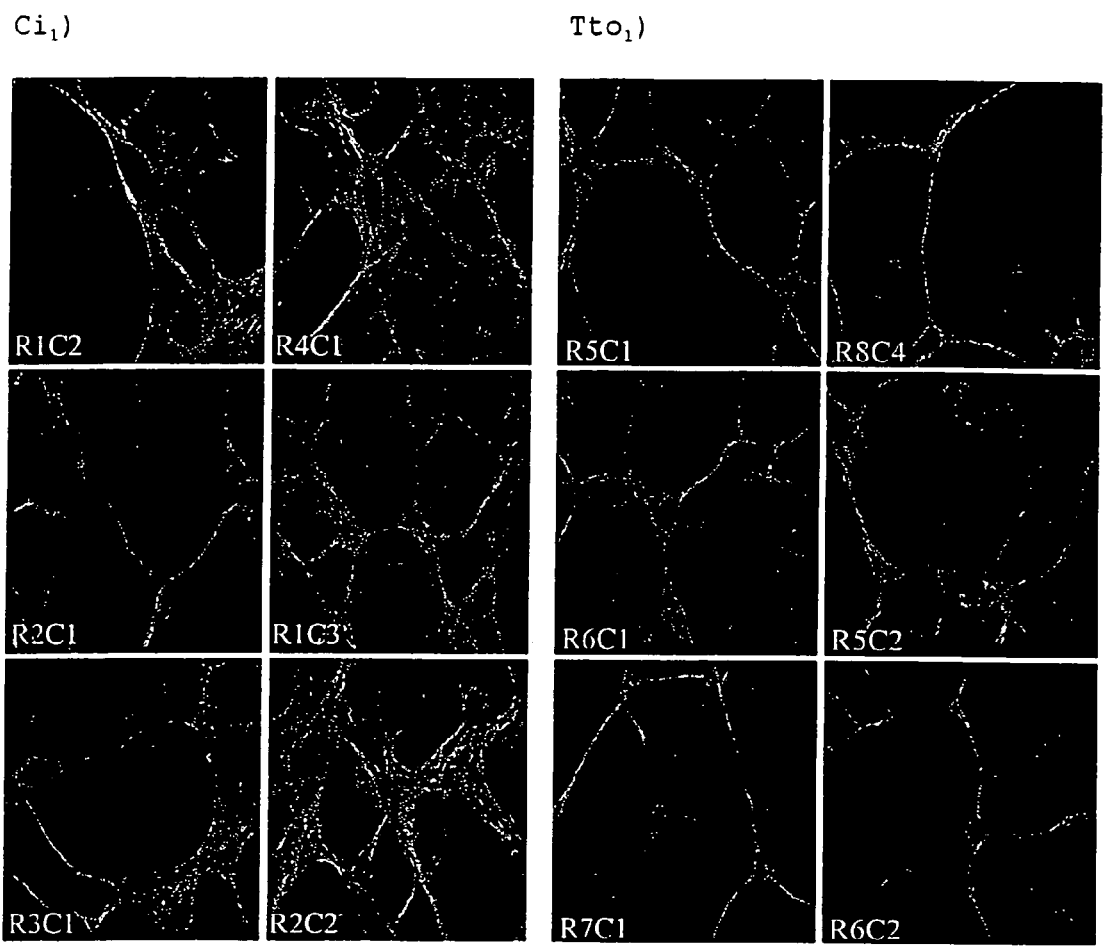
FIG. 27. Images that are representative of the 24 fields obtained by light microscopy (10x) from rat liver preparations stained with Sirius Red. Cirrhotic rats (Ci$_1$) at the end of induction of cirrhosis with CCl$_4$ and cirrhotic rats treated (Tto$_1$) with peptide P144 during induction of cirrhosis with CCl$_4$. Different fields were taken from the preparations obtained from each animal (R=rat and C=field). Polarized light and a green filter were used in order to show up the collagen fibres.

FIGS. 26 and 27 show the images obtained by light microscopy from liver preparations stained with Sirius Red at a magnification of 10× obtained from livers of rats treated during the cirrhosis induction process ($Ci_1$ and $Tto_1$).

The images in FIG. 26 were obtained without employing any type of filter.

FIG. 27 shows the images once they had been modified for investigation using special software. These modifications consist of application of two filters, one of polarized light and the other of green light, for the purpose of improving the quality of the images and facilitating automated examination of them.

FIGS. 26 and 27 reveal that there are differences between the images obtained from the cirrhotic rats ($Ci_1$) and those obtained from the rats treated with peptide P144 ($Tto_1$).

The differences in effectiveness between protocols 1 and 2 might be due to the fact that production of TGFβ1 might be much less once cirrhosis is induced (protocol 2) than during the process of induction of cirrhosis with $CCl_4$ (protocol 1), and might even be at normal levels, so that the effect of treatment with peptide P144 would be less pronounced in protocol 2 than in protocol 1.

Figure 28:
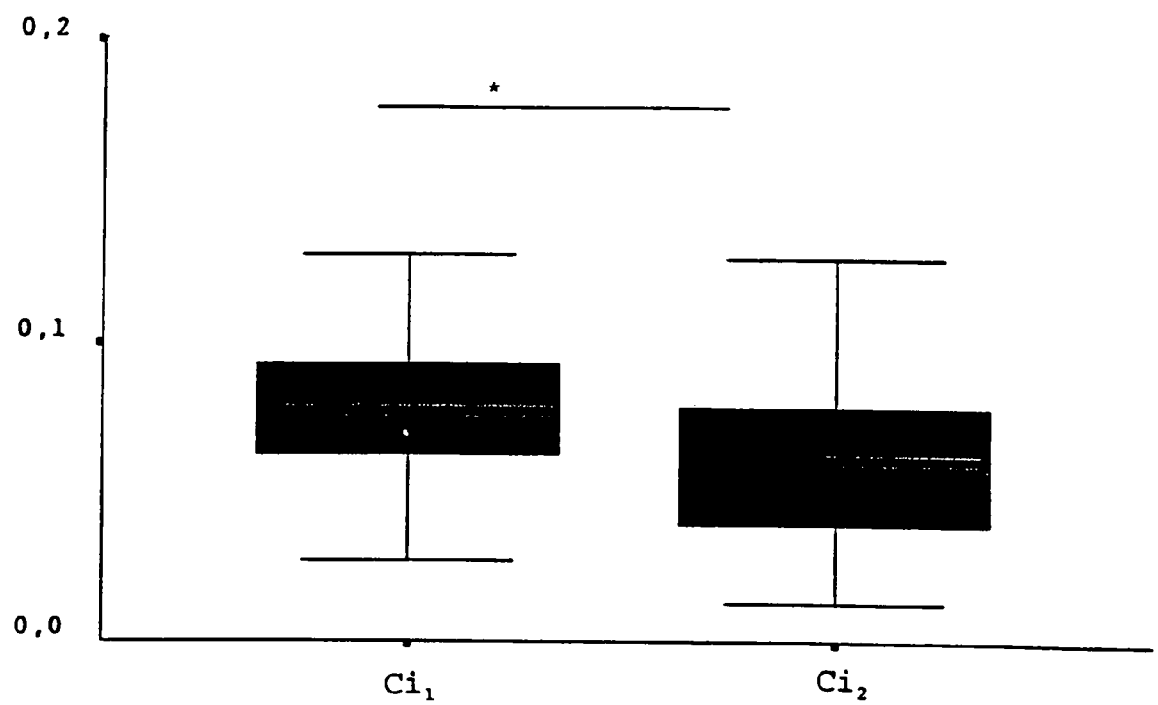
FIG. 28. Comparison between the two groups of untreated cirrhotic rats. Ci$_1$ are cirrhotic rats at the end of the 12 weeks of induction of cirrhosis with CCl$_4$, Ci$_2$ are cirrhotic rats at 4 weeks from the end of the process of induction of cirrhosis. P=0.016. Ordinate: Area of fibrosis/Total area.

When we compare the groups of untreated cirrhotic rats, at the end of the process of induction of cirrhosis ($Ci_1$) with the untreated cirrhotic rats at 4 weeks from the end of induction ($Ci_2$), we find that there are significant differences (P=0.016) between the two groups (FIG. 28), which would indicate that there is partial regression of cirrhosis when the cirrhotizing agent is removed, an observation that has been published by various authors (Szende-B et al. (1992) In Vivo 6:355–361; Columbano A (1996) Carcinogenesis 17:395–400).

These differences in effectiveness between the two protocols might also be due to the protocol itself, since the animals of protocol 2 are only treated for 3 weeks on alternate days, whereas the animals of protocol 1 are treated for a longer period of time (7 weeks, also on alternate days).

The results obtained demonstrate that it is possible to inhibit TGFβ1 both in vitro and in vivo by means of synthetic peptides derived from different proteins. In future it would be of great interest to try to increase the biological activity of these peptides. This might be accomplished by systematically replacing each of the amino acids of their sequences by the other 19. Once the peptide with greater activity was achieved it would be necessary to prepare mimotopes (McConnell-S J (1994) Gene 151:115–118; Steward-M W (1995) J. Virol. 69:7668–7673) thereof with the aim of increasing the average life of the inhibitory agent in the organism.

The invention claimed is:

1. An isolated peptide consisting of an amino acid sequence selected from the group consisting of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9 and SEQ ID NO: 10.

2. The isolated peptide of claim 1, wherein the amino acid sequence is SEQ ID NO: 3.

3. The isolated peptide of claim 1, wherein the amino acid sequence is SEQ ID NO: 4.

4. The isolated peptide of claim 1, wherein the amino acid sequence is SEQ ID NO: 5.

5. The isolated peptide of claim 1, wherein the amino acid sequence is SEQ ID NO: 6.

6. The isolated peptide of claim 1, wherein the amino acid sequence is SEQ ID NO: 7.

7. The isolated peptide of claim 1, wherein the amino acid sequence is SEQ ID NO: 8.

8. The isolated peptide of claim 1, wherein the amino acid sequence is SEQ ID NO: 9.

9. The isolated peptide of claim 1, wherein the amino acid sequence is SEQ ID NO: 1.

10. The isolated peptide of claim 1, wherein the amino acid sequence is SEQ ID NO: 2.

11. The isolated peptide of claim 1, wherein the amino acid sequence is SEQ ID NO: 10.

* * * * *